US009636299B2

(12) United States Patent
Bhattacharjee

(10) Patent No.: US 9,636,299 B2
(45) Date of Patent: May 2, 2017

(54) METHOD FOR TREATING DIABETIC RETINOPATHY

(71) Applicant: XAVIER UNIVERSITY OF LOUISIANA, New Orleans, LA (US)

(72) Inventor: Partha S. Bhattacharjee, New Orleans, LA (US)

(73) Assignee: XAVIER UNIVERSITY OF LOUISIANA, New Orleans, LA (US)

( * ) Notice: Subject to any disclaimer, the term of this patent is extended or adjusted under 35 U.S.C. 154(b) by 0 days.

(21) Appl. No.: 14/388,412

(22) PCT Filed: Mar. 15, 2013

(86) PCT No.: PCT/US2013/031911
§ 371 (c)(1),
(2) Date: Sep. 26, 2014

(87) PCT Pub. No.: WO2013/148305
PCT Pub. Date: Oct. 3, 2013

(65) Prior Publication Data
US 2015/0045296 A1    Feb. 12, 2015

Related U.S. Application Data

(60) Provisional application No. 61/617,269, filed on Mar. 29, 2012, provisional application No. 61/679,480, filed on Aug. 3, 2012.

(51) Int. Cl.
*A61K 9/00* (2006.01)
*A61K 38/17* (2006.01)

(52) U.S. Cl.
CPC ........ *A61K 9/0048* (2013.01); *A61K 38/1709* (2013.01)

(58) Field of Classification Search
CPC .......................... A61K 38/1709; A61K 9/0048
See application file for complete search history.

(56) References Cited

U.S. PATENT DOCUMENTS 7,691,382 B2    4/2010  Dobson

FOREIGN PATENT DOCUMENTS

WO    WO 2007038453 A2 *  4/2007  ............. A61K 31/00

OTHER PUBLICATIONS

Paolo S. Silva, Diabetic Retinopathy: Effect of Medications on Onset and Progression : Antiangiogenic Agents, MedScape Multispecialty, 2010, pp. 1-2.*
Ning Cheung, Diabetic retinopathy, Lancet 2010; 376: 124-36.*
International Search Report from corresponding PCT/US2013/031911, mailed Jul. 2013.

Bhattacharjee et al., "A novel peptide derived from human apolipoprotein E is an inhibotor of tumor growth and ocular angiogenesis," PLoS One. vol. 6, No. 1, Article No. e15905, 2011, pp. 1-9.
Schulter et al., "Impact of apolipoprotein(a) on in vitro angiogenesis," Arteriosclerosis, Thrombosis, and Vascular Biology. vol. 21, No. 3, 2001, pp. 433-438.
Usui et al., "Gene expression profile in corneal neovascularization identified by immunology related macroarray," Molecular Vision. vol. 10, 2004, pp. 832-836.
Conley et al., "Candidate gene analysis suggests a role for fatty acid biosynthesis and regulation of the complement system in the etiology of age-related maculopathy," Human Molecular Genetics, vol. 14, No. 14, 2005, pp. 1991-2002.
Bhattacharjee et al., "High-glucose-induced endothelial cell injury is inhibited by a peptide derived from human apolipoprotein E", PLoS One, vol. 7, No. 12, Article No. e52152, Dec. 19, 2012, pp. 1-8.
Anderson DH, Ozaki S, Nealon M, Neitz J, Mullins RF, Hageman GS, Johnson LV. Local cellular sources of apolipoprotein E in the human retina and retinal pigmented epithelium: implications for the process of drusen formation. Am J Ophthalmol. 2001;131(6):767-81.
Bhatt LK, Addepalli V. Attenuation of diabetic retinopathy by enhanced inhibition of MMP-2 and MMP-9 using aspirin and minocycline in streptozotocin-diabetic rats. Am J Transl Res. 2010;2(2):181-9.
Bhattacharjee PS, Huq TS, Mandal TK, Graves RA, Muniruzzaman S, Clement C, McFerrin HE, Hill JM. A novel peptide derived from human apolipoprotein E is an inhibitor of tumor growth and ocular angiogenesis. PLoS One. 2011;6(1):e15905.
Dredge K, Hammond E, Handley P, Gonda TJ, Smith MT, Vincent C, Brandt R, Ferro V, Bytheway I. PG545, a dual heparanase and angiogenesis inhibitor, induces potent anti-tumour and anti-metastatic efficacy in preclinical models. Br J Cancer. 2011;104(4):635-42.
Dyer CA, Cistola DP, Parry GC, Curtiss LK. Structural features of synthetic peptides of apolipoprotein E that bind the LDL receptor. J Lipid Res. 1995;36(1):80-8.
Elkin M, Ilan N, Ishai-Michaeli R, Friedmann Y, Papo O, Pecker I, Vlodavsky I. Heparanase as mediator of angiogenesis: mode of action. FASEB J. 2001;15(9):1661-3.
Fong DS, Aiello LP, Ferris FL 3rd, Klein R. Diabetic retinopathy. Diabetes Care. 2004;27(10):2540-53.
Huet E, Vallée B, Delbé J, Mourah S, Pruliere-Escabasse V, Tremouilleres M, Kadomatsu K, Doan S, Baudouin C, Menashi S, Gabison EE. EMMPRIN modulates epithelial barrier function through a MMP-mediated occludin cleavage: implications in dry eye disease. Am J Pathol. 2011;179(3):1278-86.
Ji ZS, Fazio S, Mahley RW. Variable heparan sulfate proteoglycan binding of apolipoprotein E variants may modulate the expression of type III hyperlipoproteinemia. J Biol Chem. 1994;269(18):13421-8.
Kelly BA, Neil SJ, McKnight A, Santos JM, Sinnis P, Jack ER, Middleton DA, Dobson CB. Apolipoprotein E-derived antimicrobial peptide analogues with altered membrane affinity and increased potency and breadth of activity. FEBS Journal. 2007;274(17):4511-4525.

(Continued)

*Primary Examiner* — Hasan Ahmed
*Assistant Examiner* — Erinne Dabkowski
(74) *Attorney, Agent, or Firm* — McBee Moore Woodward & Vanik IP, LLC

(57) ABSTRACT

Compositions useful for treatment of retinal pathologies, including diabetic retinopathy, and methods of making and using said compositions, are provided.

2 Claims, 15 Drawing Sheets

(56) References Cited

OTHER PUBLICATIONS

Klein R, Davis MD, Moss SE, Klein BE, Demets DL. The Wisconsin Epidemiologic Study of Diabetic Retinopathy. A comparison of retinopathy in younger and older onset diabetic persons. Adv Exp Med Biol. 1985;189:321-35.

Kowal RC, Herz J, Goldstein JL, Esser V, Brown MS. Low density lipoprotein receptor-related protein mediates uptake of cholestelyl esters derived from apoprotein E-enriched lipoproteins. Proc. Natl. Acad. Sci. U.S.A. 1989;86(15):5810-4.

Kowluru RA. Role of matrix metalloproteinase-9 in the development of diabetic retinopathy and its regulation by H-Ras. Invest Ophthalmol Vis Sci. 2010;51(8):4320-6.

Mahley RW. Apolipoprotein E: cholesterol transport protein with expanding role in cell biology. Science. 1988;240 (4852):622-30.

Miyamoto K, Khosrof S, Bursell SE, Moromizato Y, Aiello LP, et al. Vascular endothelial growth factor (VEGF)-induced retinal vascular permeability is mediated by intercellular adhesion molecule-1 (ICAM-1). Am J Pathol. 2000;156:1733-1739.

Parish CR, Freeman C, Hulett MD. Heparanase: a key enzyme involved in cell invasion. Biochim Biophys Acta. 2001;1471(3):M99-108.

Raman K, Ninomiya M, Nguyen TK, Tsuzuki Y, Koketsu M, Kuberan B. Novel glycosaminoglycan biosynthetic inhibitors affect tumor-associated angiogenesis. Biochem Biophys Res Commun. 2011;404(1):86-9.

Rao R. Occludin phosphorylation in regulation of epithelial tight junctions. Ann N Y Acad Sci. 2009;1165:62-8.

Weisgraber KH, Innerarity TL, Rall SC JR, Manley RW. Receptor interactions controlling lipoprotein metabolism. Can J Biochem Cell Biol. 1985;63(8):898-905.

Xu HZ, Le YZ. Significance of outer blood-retina barrier breakdown in diabetes and ischemia. Invest Ophthalmol Vis Sci. 2011;52(5):2160-4.

\* cited by examiner

METHOD FOR TREATING DIABETIC RETINOPATHY

CROSS-REFERENCE TO RELATED APPLICATIONS

This application is a §371 National Stage application of PCT/US2013/031911, filed 15 Mar. 2013, which claims the benefit of U.S. Provisional Patent Application No. 61/617,269, filed on 29 Mar. 2012, and U.S. Provisional Patent Application No. 61/679,480, filed 3 Aug. 2012, all of which are hereby incorporated by reference in their entirety.

BACKGROUND

1. Field

The present disclosure relates to compositions useful for treatment of retinal pathologies, including diabetic retinopathy, and to methods of making and using said compositions.

2. Description of Related Art

Diabetes mellitus is characterized by hyperglycemia (high glucose in the blood), which results either from insufficient production of insulin (type 1 diabetes) or from a cellular insensitivity to insulin in the blood. Diabetic retinopathy is a severe complication of diabetes, affecting the vision of more than half of adult diabetics, and is the leading cause of blindness in adults in the United States (1). The mechanisms of diabetic retinopathy and therapeutic strategies for treating it are the subject of extensive efforts. In a clinical setting, for example, laser photocoagulation and anti-angiogenic therapy represent state-of-the-art therapeutic strategies for inducing angiogenic regression and reduction of macular edema. Nevertheless, therapeutic challenges remain because many patients are unresponsive to current therapeutic approaches and/or because the state-of-the-art anti-angiogenic and photocoagulation therapies are accompanied by significant side-effects.

Diabetic hyperglycemia is thought to cause injury to endothelial cells that line retinal blood vessels, resulting in inflammation and neovascularization (growth of new blood vessels), which are characteristic of diabetic retinopathy. Extracellular matrix (ECM) is a cementing substance that supports and maintains the integrity of cells, including retinal endothelial cells. Hyperglycemia induces retinal endothelial cells to increase the production of ECM-degrading enzymes, including heparanase and matrix metalloproteinases (MMPs). Heparanase degrades the ECM by degrading heparan sulfate moieties into shorter-length oligosaccharides, while MMPs are zinc-dependent endopeptidases that also degrade ECM. Hyperglycemia-induced amplification of heparanase and MMP production results in inflammation and dysregulation of the blood-retinal barrier (BRB), leading to neovascularization and/or leakage of retinal blood vessels (diabetic macular edema). Strategies targeting ECM-degrading enzymes could be therapeutically beneficial for treatment of diabetic retinopathy, yet success has remained elusive.

Heparanase is implicated in angiogenesis, inflammation and metastasis (15). It is synthesized as a 65 kDa inactive precursor that undergoes proteolytic cleavage, yielding a 50 kDa active unit (9). Upregulated expression of heparanase was reported in vitro in human RE cells exposed to elevated levels of glucose, and in streptozotocin-induced diabetic rats in vivo. Heparanase inhibitors can be anti-angiogenic (9). A drug known as PI-88 (Phosphomannopentose sulfate-88) is currently under Phase II and III clinical trials known to function as a competitive inhibitor of heparanase. PI-88 is known to inhibit tumor angiogenesis and metastasis. However, dose-limiting toxicity of PI-88 is reported to inhibit thrombin-induced platelet aggregation and to prolong anticoagulant activities. Heparanase is known to play many important roles in the regulation of several aspects of cancer biology, including angiogenesis, tumor progression, and metastasis (9). Heparanase is an endo-β-D-glucuronidase that degrades HS-proteoglycans (HSPG) in the extracellular matrix (EM) and the basement membrane. The angiogenic capacity of heparanase has been traditionally attributed to its ability to release HS-bound angiogenic growth factors from the ECM, such as vascular endothelial growth factor (VEGF). The use of HS mimetics to modulate these processes may therefore present a promising approach for ECM degradation-based therapies.

Matrix metalloproteinases (MMPs) are zinc-dependent ECM degrading enzymes (12). MMP regulates BRB functions of several tissues including those in the eyes. Hypergycemic injury and laser induced injury reported to elevate the expression of MMPs in the posterior eye. The increased proteolytic activity of ECM degrading enzymes facilitates the permeability changes of BRB. An inhibitor of MMPs was able to inhibit the diabetic hypoglycemia-induced BRB breakdown (12).

In the eye, various matrix-degrading enzymes including, for example, endoglycosidases and matrix metalloproteinases are thought to cause remodeling of the tight structural extracellular matrix (ECM) and basement membrane (BM) networks in response to altered microenvironments of BRB compositions. The BRB is formed by retinal endothelilal cells, and is essential for protecting the retina from harmful agents found in the blood. Retinal endothelial cells form tight junctions (TJs) that are essential to maintaining the structural integrity of the BRB. Degradation of the BRB, which may be influenced by the extracellular matrix degradation, is known to result from various causes including, for example, hyperglycemic injury or laser treatment of proliferative retinal angiogenesis (8).

ECM degradation of BRB is known to result from hyperglycemic injury or laser treatment of proliferative retinal angiogenesis. Loss of BRB integrity and leakage of plasma constituents leads to vision loss and associated microvascular complications of the posterior eye. Besides affecting the tight junction proteins, expression and activity of specific extracellular proteinases is known to change the endothelial permeability of BRB.

Impairment of the BRB tight junctions can occur through the actions of various matrix-degrading enzymes including, for example, endoglycosidases and matrix metalloproteinases (MMPs).

Endoglycosidases contribute to releasing sequestered heparan sulfate-binding proteins (e.g., VEGF and other growth factors), which are then free to signal through their cognate receptors, leading to alterations in the ECM that modulate BRB permeability and may facilitate angiogenesis. One such matrix-degrading enzyme is heparanase, an endoglycosidase that specifically cleaves the heparan sulfate (HS) side chains of HSPGs (9). Heparanase has been implicated in human cancer, particularly in malignant, aggressive tumors (9). These data have come largely from correlative studies documenting a positive association between increased heparanase expression or activity and enhanced tumor invasion and metastasis (9). The ECM remodeling role of heparanase was confirmed in several in vitro and in vivo model systems, including wound healing (9), tumor xenografts (10), Matrigel plug assay (10), and tubelike structure formation (11). Heparanase offers an attractive drug target. Species of heparin and heparin/HS-mimicking compounds that inhibit the enzyme may prevent undesirable vascular remodeling. The matrix metalloproteinase's (MMPs) are zinc-dependent ECM-derading enzymes. MMPs regulate the functions of several tissues including those in the eyes (12) including, for example, the BRB.

Apolipoprotein E (apoE) is a protein that was first recognized for its importance in the metabolism of lipoproteins and its role in cardiovascular disease. Subsequent research has demonstrated the involvement of apoE in various biological processes including, for example, Alzheimer's disease, immunoregulation, and cognition. Human apoE is initially synthesized as a propeptide of 317 amino acids. Following post-translational cleavage of an 18 amino acid ("a.a.") signal peptide, mature apoE is secreted as a 34.2 kDa protein consisting of 299 amino acids. ApoE is a single-chain protein containing two independently folded functional domains—a 22-kDa N-terminal domain (a.a. residues 1-191) and a 10-kDa C-terminal domain (a.a. residues 222-299)—and is a ligand for cell-surface heparan sulfate proteoglycan (HSPG) (2,3). The N- and C-terminal domains of apoE each contain a heparin binding site (13). The N-terminal domain heparin binding site is located between residues 142-147, within the apoE heparan sulfate binding region (see SEQ ID NO: 2), and overlaps the receptor binding region of SEQ ID NO:1 (3). In fact, the HSPG binding activity of apoE variants is significantly decreased by mutations of Arg-142, Arg-145, and Lys-146, indicating that these basic amino acid residues contribute to binding of both heparin and heparan sulfate proteoglycan (4). A tandem repeat dimer peptide derived from apoE residues 141-149 reportedly bears anti-inflammatory and anti-angiogenic activity in vivo against herpes virus infection (5); the tandem repeat may reflect increased adoption of α-helical structure and improved stability (6). ApoE is expressed in almost all cells, including retinal endothelial (RE) cells, and the degree of apoE expression in the retina is almost equal to that observed in the brain (7).

Treatment with a human apolipoprotein E derived dimer peptide (apoEdp) blocks VEGF-induced ocular angiogenesis in a rabbit eye model (17). The heparan sulfate (HS) binding domain of human apolipoprotein E (apoE) possesses anti-tumorigenic and anti-angiogenic roles through inhibition of vascular endothelial growth factor (VEGF), but whether this peptide has a vascular remodeling role through inhibition of ECM degrading enzyme heparanase is unknown.

The solution to these technical problems is provided by the embodiments characterized in the claims.

BRIEF SUMMARY

Currently, no non-invasive techniques for the treatment of diabetic retinopathy are available. This invention is focused on non-invasive topical eye drop treatment of diabetic retinopathy using a peptide that mimics human apolipoprotein E.

The subject disclosure features, in one embodiment, a method for treating retinopathy in a mammal in need thereof, the method comprising providing a composition comprising apoEdp, an active analogue of apoEdp, or a combination thereof to said mammal. In one aspect of this embodiment, the composition is provided as an ophthalmic preparation. In one aspect, said providing comprises topical ocular administration, retrobulbar administration, intraocular administration, oral administration, intravenous administration, intraperitoneal administration, intramuscular administration, subcutaneous administration, subconjunctival administration, or a combination thereof. In one aspect, the retinopathy may be diabetic retinopathy.

In one embodiment, the disclosure features a method for treating diabetic retinopathy, ocular angiogenesis, retinal edema, and combinations thereof comprising topically applying to an eye that exhibits, is diagnosed with, or is at risk of developing diabetic retinopathy, ocular angiogenesis, retinal edema, or combinations thereof a composition comprising apoEdp or SEQ ID NO:3, an active analogue of apoEdp or SEQ ID NO:3, or a combination thereof to said eye.

The subject disclosure features, in another embodiment, a method for treating angiogenesis in a mammal in need thereof, the method comprising providing a composition comprising apoEdp, an active analogue of apoEdp, or a combination thereof to said mammal. In one aspect of this embodiment, the angiogenesis is intraocular angiogenesis. In one aspect of this embodiment, the intraocular angiogenesis is retinal angiogenesis. In one aspect, the composition is an ophthalmic preparation. In one aspect, the preparation is provided via topical administration, retrobulbar administration, intraocular administration, oral administration, intravenous administration, intraperitoneal administration, intramuscular administration, subcutaneous administration, subconjunctival administration, or a combination thereof.

The subject disclosure features, in another embodiment, a composition comprising apoEdp, an active analogue of apoEdp, or a combination thereof for use in treating a disease selected from the group consisting of ocular angiogenesis, diabetic retinopathy, retinal edema, and combinations thereof. In one aspect, the disclosure features a composition comprising apoEdp, an active analogue of apoEdp, or a combination thereof for use in treating an eye that exhibits, is diagnosed with, or is at risk of developing diabetic retinopathy, ocular angiogenesis, retinal edema, or combinations thereof.

The subject disclosure features, in one embodiment, a method for treating retinopathy in a mammal in need thereof, the method comprising providing a composition comprising SEQ ID NO:3, an active analogue of SEQ ID NO:3, or a combination thereof to said mammal. In one aspect of this embodiment, the composition is provided as an ophthalmic preparation. In one aspect, said providing comprises topical ocular administration, retrobulbar administration, intraocular administration, oral administration, intravenous administration, intraperitoneal administration, intramuscular administration, subcutaneous administration, subconjunctival administration, or a combination thereof. In one aspect, the retinopathy may be diabetic retinopathy.

The subject disclosure features, in another embodiment, a method for treating angiogenesis in a mammal in need thereof, the method comprising providing a composition comprising SEQ ID NO:3, an active analogue of SEQ ID NO:3, or a combination thereof to said mammal. In one aspect of this embodiment, the angiogenesis is intraocular angiogenesis. In one aspect of this embodiment, the intraocular angiogenesis is retinal angiogenesis. In one aspect, the composition is an ophthalmic preparation. In one aspect, the preparation is provided via topical administration, retrobulbar administration, intraocular administration, oral administration, intravenous administration, intraperitoneal administration, intramuscular administration, subcutaneous administration, subconjunctival administration, or a combination thereof.

The subject disclosure features, in another embodiment, a composition comprising SEQ ID NO:3, an active analogue of SEQ ID NO:3, or a combination thereof for use in treating a disease selected from the group consisting of ocular angiogenesis, diabetic retinopathy, retinal edema, and combinations thereof. In one aspect, the disclosure features a composition comprising SEQ ID NO:3, an active analogue of SEQ ID NO:3, or a combination thereof for use in treating an eye that exhibits, is diagnosed with, or is at risk of developing diabetic retinopathy, ocular angiogenesis, retinal edema, or combinations thereof.

In one aspect, the apoEdp or SEQ ID NO:3 is provided at a concentration of from about 0.01% (w/v) to about 20% (w/v), from about 0.05% (w/v) to about 15% (w/v), from about 0.1% (w/v) to about 10% (w/v), from about 0.25% (w/v) to about 5% (w/v), from about 0.5% (w/v) to about 2.5% (w/v), from about 0.75% (w/v) to about 1% (w/v), and preferably about 1% (w/v). Alternatively, the apoEdp or SEQ ID NO:3 is provided at a dose of from about 1 to about 500, from about 1 to about 250, from about 1 to about 100, from about 1 to about 75, from about 1 to about 50, from about 1 to about 40, from about 1 to about 20, preferably from about 25 to about 75, and more preferably from about 35 to about 65 mg/kg/day.

BRIEF DESCRIPTION OF THE SEQUENCES

SEQ ID NO:1 represents amino acids 133-150 of mature apoE, corresponding to the receptor binding domain.

SEQ ID NO:2 represents amino acids 133-149 of mature apoE, corresponding to heparan sulfate binding domain.

SEQ ID NO:3 represents the apoEdp amino acid sequence.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements.

DETAILED DESCRIPTION

Figure 1:
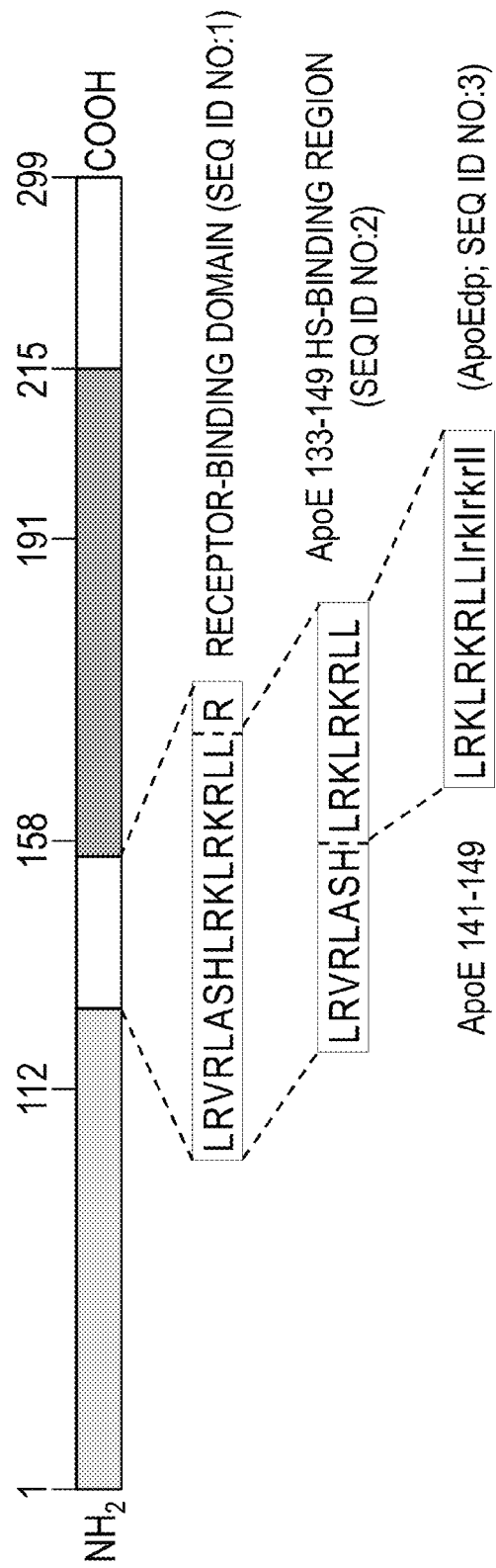
FIG. 1 is a schematic representation of human apoE protein, the receptor binding domain of apoE (LRVRLASHLRKLRKRLLR (SEQ ID NO: 1)), the heparan sulfate binding region of apoE ILRVRLASHLRKLRKRLL (SEQ ID NO: 2)), and apoEdp ILRKLRKRLLlrklrkrll (SEQ ID NO: 3)).

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this disclosure belongs.

The phrase "active analogue thereof" refers to an analogue of the peptide that is known to have activity, such as those described in Kelley et al., 2007 (16). Analogues of apoEdp have been reported (16), and it is well within the abilities of those of ordinary skill in the art to modify apoEdp to create an analogue and then test it to confirm that it retains the desired activity (e.g., corneal permeability and activity against diabetic retinopathy, angiogenesis, etc.).

The term "effective amount" as used herein and in the claims refers to an amount of apoEdp (SEQ ID NO:3) or an active analogue thereof sufficient to prevent, ameliorate or lessen the damage caused to a mammalian retina by diabetes, such as that resulting from diabetic retinopathy, retinal inflammation, retinal edema, angiogenesis, and combinations thereof to a statistically significant degree (p<0.05). The term therefore includes, for example, an amount sufficient to lessen the severity of damage to a mammalian retina by 25%, preferably by 50%, and most preferably by 90%. The dose ranges for administration of apoEdp are those that produce the desired effect, and include from about 0.01% (w/v) to about 20% (w/v), from about 0.05% (w/v) to about 15% (w/v), from about 0.1% (w/v) to about 10% (w/v), from about 0.25% (w/v) to about 5% (w/v), from about 0.5% (w/v) to about 2.5% (w/v), from about 0.75% (w/v) to about 1% (w/v), and preferably about 1% (w/v). A person of ordinary skill in the art, given the teachings of the present specification, may readily determine suitable dose ranges.

The dose can be adjusted by the individual physician in the event of any contraindications or sequelae. The preferred application is topical.

Pharmaceutically acceptable carrier preparations for administration of apoEdp include sterile, aqueous or non-aqueous solutions, suspensions, and emulsions. Examples of nonaqueous solvents are propylene glycol, polyethylene glycol, glycerol, vegetable oils such as olive oil, and injectable organic esters such as ethyl oleate. Aqueous carriers include water, emulsions or suspensions, including saline and buffered media. The active therapeutic ingredient may be mixed with excipients that are pharmaceutically acceptable and are compatible with the active ingredient. Suitable excipients include water, saline, dextrose, and glycerol, or combinations thereof. Preservatives and other additives may also be present such as, for example, antimicrobials, antioxidants, chelating agents, inert gases, and the like.

Figure 2:
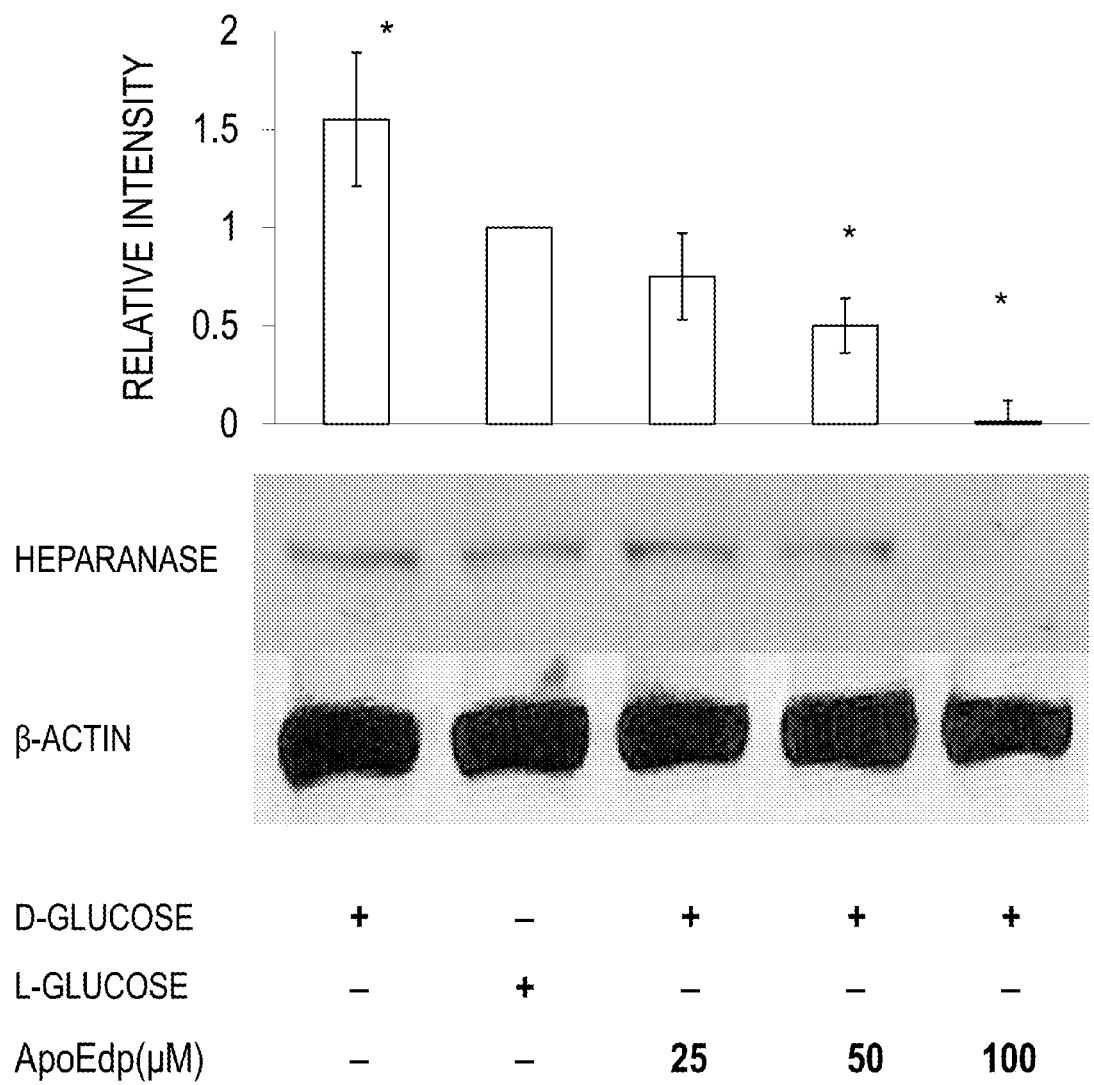
FIG. 2 shows that apoEdp inhibits high glucose-induced expression of heparanase in human retinal endothelial cells.
Figure 3:
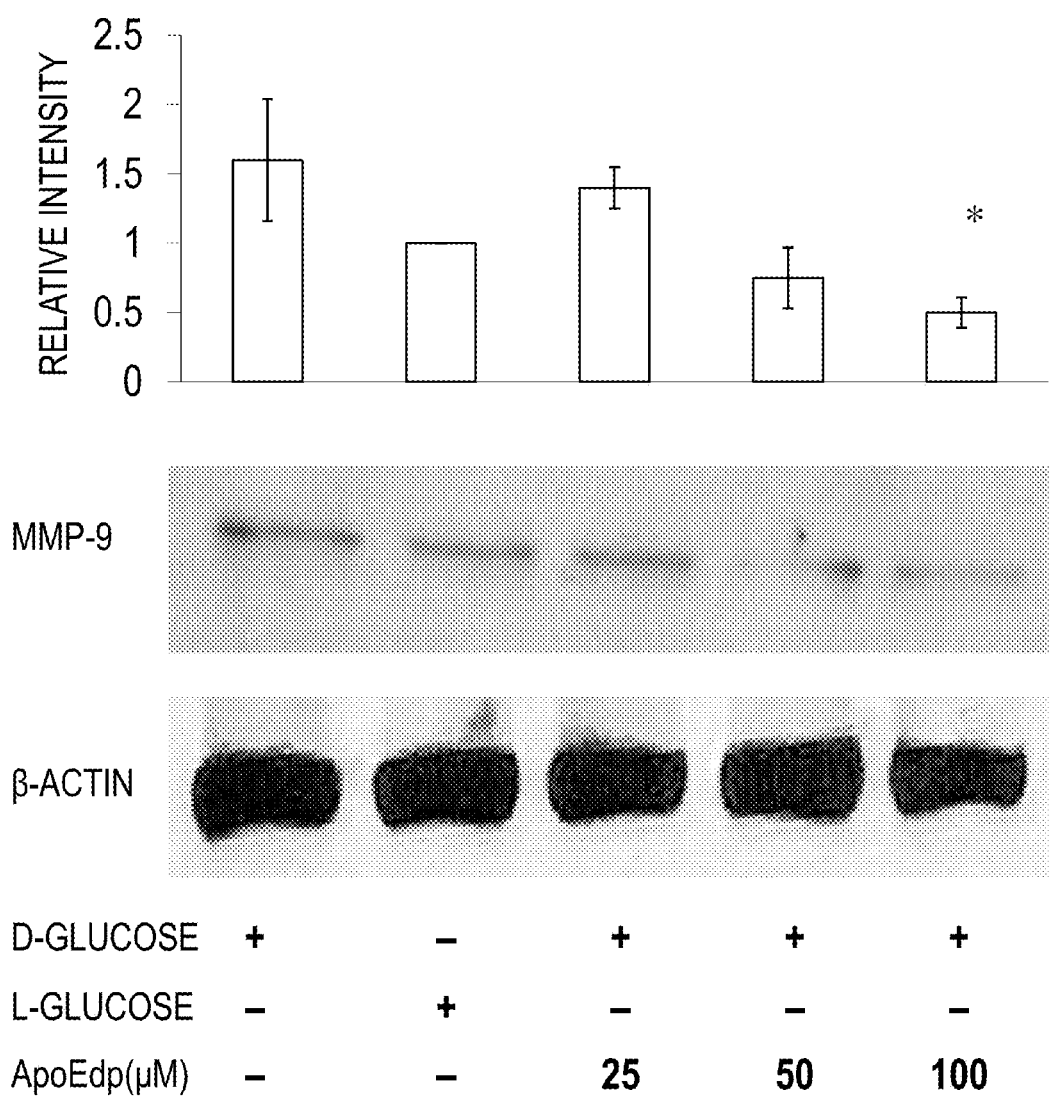
FIG. 3 shows that apoEdp inhibits high glucose-induced expression of MMP9 in human retinal endothelial cells.

The instant invention is focused on treating retinal pathologies associated with diabetes. The present results demonstrate that exposure of human retinal endothelial cells to elevated levels of glucose in vitro induces increased expression of heparanase (FIG. 2), MMP9 (FIG. 3), Aheparan sulfate (FIG. 4), and endothelial nitric oxide synthase (FIG. 6), each of which can be suppressed by administering apoEdp (EXAMPLE 2 and FIGS. 2, 3, 4 & 6, respectively). The results also demonstrate that human retinal endothelial cells co-incubated with 100 μM apoEdp and 30 mM glucose express greater levels of occludin than cells incubated with 30 mM glucose alone (FIG. 5) The instant results also show that apoEdp is a cornea-penetrating peptide that migrates into the aqueous and vitreous chambers when applied topically to the cornea (EXAMPLE 3 & TABLE 1). Thus, the results suggest that heparanase, MMPs, heparan sulfate, eNOS, and occludin—all of which are thought to play roles in diabetic retinopathy—can be effectively modulated by apoEdp treatment in vitro and in vivo. In mouse eyes, laser photocoagulation induced retinopathy caused elevated expression of heparanase and MMPs, which was inhibited by intraperitoneal injection of apoEdp (see FIG. 8). Experiments have also been conducted to determine the effects of a non-invasive topical apoEdp eye drop treatment in diabetic mice. Either topical eye drop treatment of 1% apoEdp 4 times a day or intraperitoneal injection (40 mg/kg) of apoEdp daily for 14 days in an in vivo mouse model of streptozotocin-induced diabetes, inhibited the loss of tight junction proteins occludin and zona occludin-1 (ZO-1). These findings imply a functional relationship between apoE and endothelial cell matrix suggesting the interaction of these molecules can be inhibited by a short peptide derived from the receptor-binding region of apoE. Unlike intact apoE protein, which consists of 299 amino acid residues and demonstrates minimal penetration through corneas, the small (18 amino acid residues) apoE-mimetic peptide apoEdp can penetrate the corneas to attain high aqueous humor concentration (see, e.g., TABLE 1). The data herein demonstrate that topical eye drop application of a composition comprising apoEdp can cross mouse cornea to aqueous humor within three hours of application. This result suggests that a similar outcome would be observed in other mammalian eyes, including human eyes.

Because upregulation of heparanase leads to cleavage of HSPG, which is then believed to lead to growth factor mobilization and remodeling of the ECM in the BRB, inhibition of heparanase activity is expected to antagonize BRB impairment.

Methods

Cell Culture. Primary cultures of human retina microvascular endothelial cells (hRMECs) were purchased from the Applied Cell Biology Research Institute and grown on attachment factor-coated plates in cell systems complete (CSC) medium (Cell Systems, Kirkland, Wash.) supplemented with 20% fetal bovine serum, culture boost (animal derived growth factors) and bac-off (antibiotics). The primary hRMECs were used in their passages 4 to 6. The 18-a.a. apoE mimetic peptide apoEdp (SEQ ID NO:3, Ac-LRKLRKRLLLRKLRKRLL-amide), derived from the human apolipoprotein E receptor-binding region (see SED ID NO:1) between residues 141 and 149, was synthesized (Genemed, Arlington, Tex.) with a purity of greater than 95%. The apoEdp peptide was dissolved in phosphate-buffered saline ("PBS") at a concentration appropriate for further experimental use. The hRMECs in vitro were incubated for 72 hours with 30 mM of either D- or L-glucose (Sigma Aldrich) in the presence or absence of different concentrations of apoEdp as shown in, for example, FIGS. 2-6.

Western Blotting. The hRMECs were harvested in M-PER Mammalian Protein Extraction Reagent (Thermo Fisher Scientific, Inc., Rockford, Ill.) containing protease inhibitor cocktail. The total protein concentration was determined using a BCA protein assay kit (Pierce, Rockford, Ill.). Equal amounts of protein were separated by electrophoresis on 5-20% SDS-polyacrylamide gels and transferred electrophoretically onto nitrocellulose membranes (Amersham, Little Chalfont, UK). The membranes were blocked for 1 hour with shaking in 5% nonfat milk, after which they were incubated overnight with shaking at 4° C. with anti-HPA-1 (human heparanase; 1:1000, Santa Cruz Biotechnology, Inc., Santa Cruz, Calif.), anti-MMP9 (human MMP9; 1:2000, Santa Cruz Biotechnology, Inc., Santa Cruz, Calif.), anti-eNOS (1:10,000, Thermo Scientific), anti-phospho-eNOS pSer1177 (1:1000, Thermo Scientific), anti-occludin (1:1000; Santa Cruz Biotechnology, Inc., Santa Cruz, Calif.) or anti-ΔHS (3G10; 1:1000, amsbio LLC, Lake Forest, Calif.). After washing with PBS-Tween 20 (PBS-T), the membranes were then incubated with horseradish peroxidase-(HRP) conjugated anti-rabbit IgG or anti-mouse IgG (1:10,000, Pierce) in PBS-T and 1% nonfat milk for 1 hour at room temperature with shaking, after which non-bound HRP-conjugate was removed by washing with PBS-T. Chemiluminescence was visualized with a SuperSignal® West Pico chemiluminescent substrate kit (Thermo Fisher Scientific, Inc., Rockford, Ill.). To ensure the equal loading of protein in each lane, each membrane was stripped and re-probed with an antibody against β-actin, and the chemiluminescence was detected as described previously. After scanning the blots with a flatbed scanner, band intensities were analyzed using ImageJ (NIH) and the relative intensity values were normalized to control values.

Laser Photocoagulation-Induced Retinopathy. Female mice (C57BL/6J), aged 6-8 weeks, were used for retinal laser photocoagulation studies. The mice were treated and maintained in accordance with the ARVO Statement for the Use of Animals in Ophthalmic and Vision Research. The mice were anesthetized by intraperitoneal injection of a mixture of ketamine (100 mg/kg; Warner Lambert Co., Morris Plains, N.J.) and xylazine (10 mg/kg; Bayer AG, Leverkusen, Germany), and the pupils dilated with 2.5% tropicamide (Alcon, Fort Worth, Tex.). Laser irradiation (532 nm; Novus Spectra ophthalmic laser, Lumenis, Inc., Santa Clara, Calif.) was delivered through a slit lamp ophthalmoscope (Model SL-07; Topcon, Inc. Tokyo, Japan)

with a handheld coverslip, floated on a drop of 2.5% methylcellulose, serving as a contact lens. The laser spots (20 spots/retina) were placed at a setting of 50-μm diameter, 100 ms duration, and 150-mW intensity and was scattered in the upper quadrant of the fundus. The left eye of each animal was laser treated, and the right eye remained untreated, serving as a control. The formation of a bubble immediately after laser application and the absence of subretinal hemorrhage was considered indicative of suitable laser burns appropriate for inclusion in the study.

Figure 7:
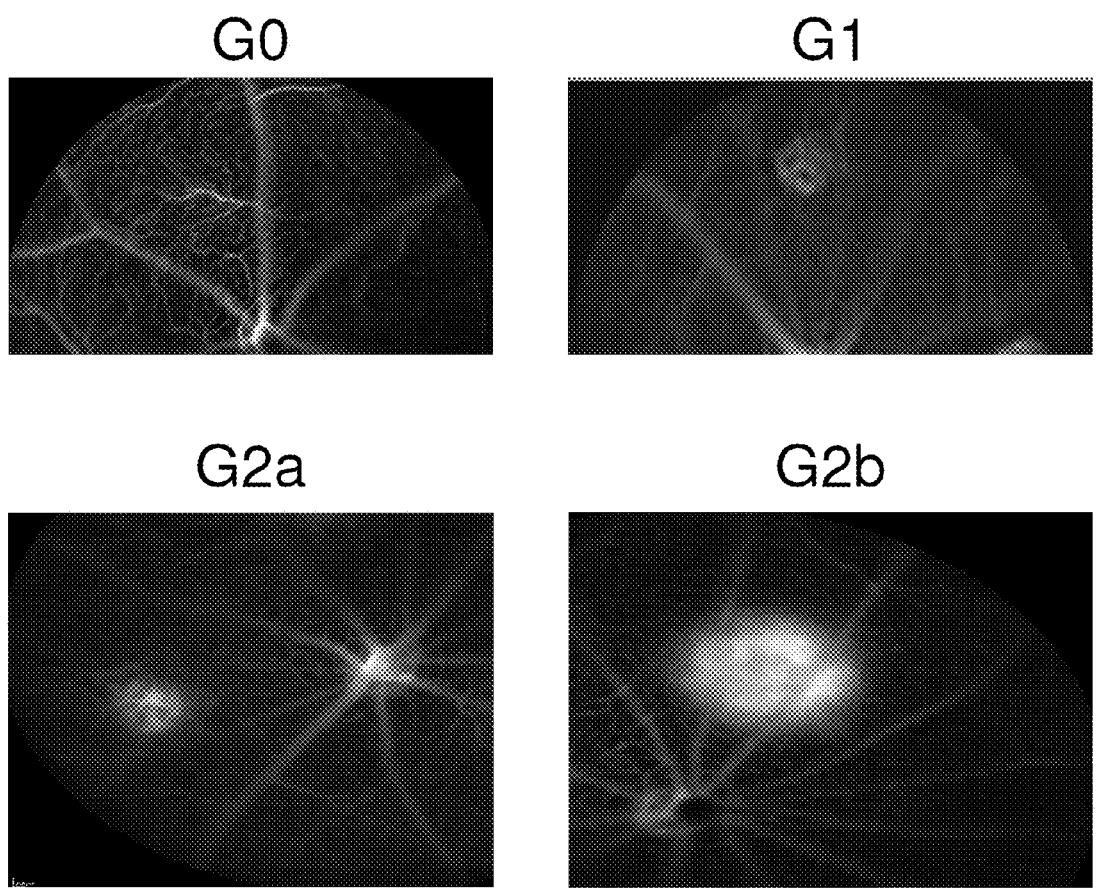
FIG. 7 shows four photographs of mouse retinas undergoing fluorescein angiography, illustrating the grading scale used for leakage cloud classification of mouse retina.

Fundus angiography. In vivo fundus angiography was conducted using a SPECTRALIS® HRA+OCT high-resolution, spectral domain optical coherence tomography imaging system (Heidelberg Engineering, Inc., Vista, Calif.), which uses a high-resolution spectral domain optical coherence scanning laser ophthalmoscope. As shown in FIG. 7, retinal images were collected and graded at 7 and 14 days following laser treatment. The terms Grade 0, Grade 1, Grade 2a, and Grade 2b are defined as follows: Grade 0 (G0)—no hyperfluorescence; Grade 1 (G1)—hyperfluorescence without leakage; Grade 2a (G2a)—hyperfluorescence and late leakage; Grade 2b (G2b)—bright hyperfluorescence and late leakage beyond treated areas (see, e.g., FIG. 7).

Figure 8:
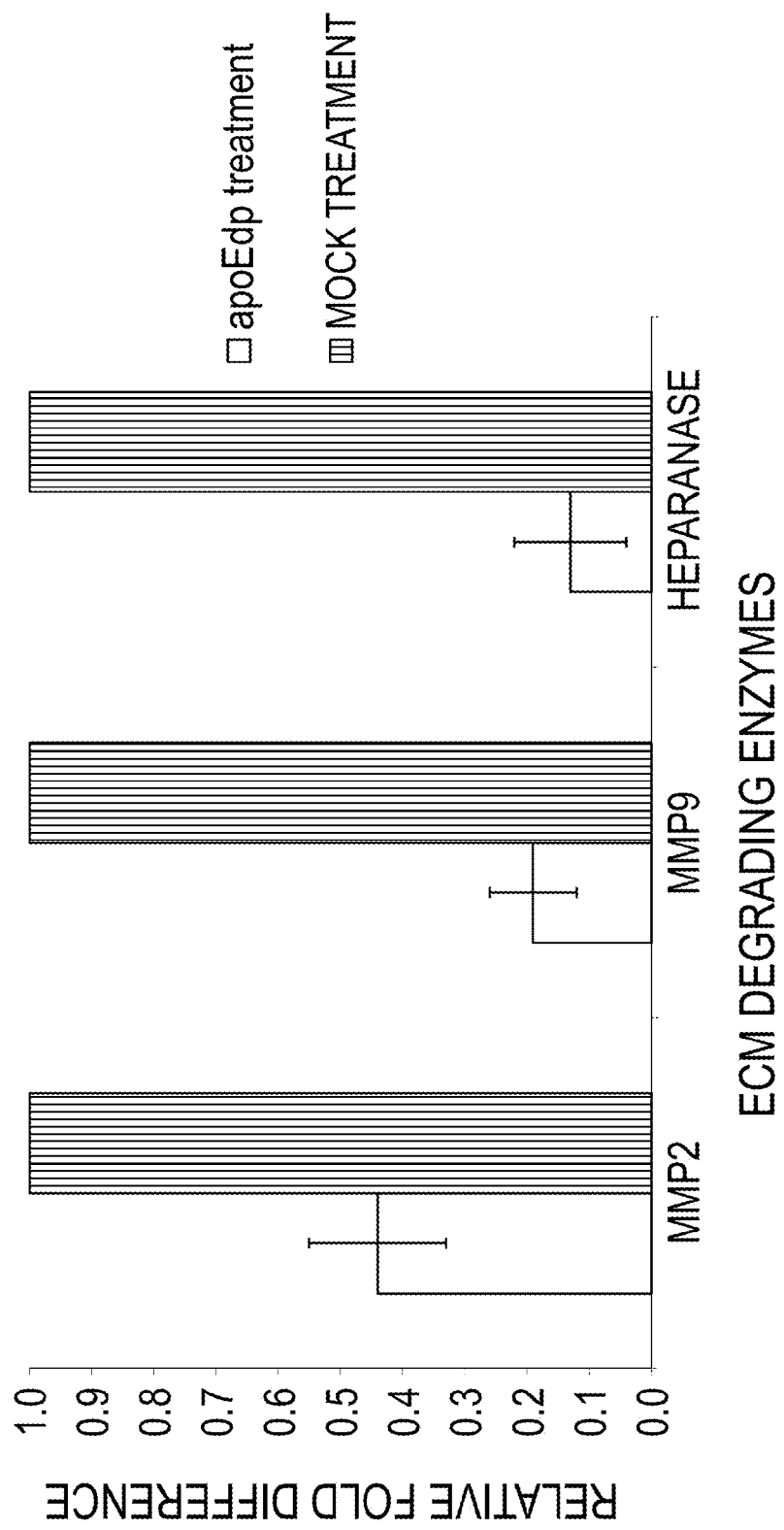
FIG. 8 shows the results of real-time RT-PCR analysis of mouse eyes exposed to laser photocoagulation induced retinopathy, in the presence or absence of apoEdp.

RNA Extraction, Reverse Transcription, & PCR. Following euthanasia, mouse eyes were enucleated and placed immediately into RNAlater® RNA stabilization reagent (Qiagen, Hilden, Germany). Intraocular fluids were aspirated and pooled, and total cellular RNA was isolated using an RNeasy® Mini Kit (Qiagen) according to the manufacturer's instructions. Gene expression was measured at RNA level per 100 ng of total RNA using one-step RT-PCR kit (Bio-Rad, Hercules, Calif.). Four host genes (mouse GAPDH, mouse MMP2, mouse HPSE-1 (heparanase-1), and mouse MMP9) were analyzed to confirm relative quantitative expression levels. The primer pairs used were specifically designed and synthesized by Qiagen GmbH, Hilden, Germany (Quantitech Primer assay kit, for each host gene, catalog numbers QT01658692, QT00088396, QT00009555, and QT00040040, respectively). One-step Real-time quantitative RT-PCR reactions were performed in a 50-μL volume containing a solution of 1× supermix (iQ SYBR Green; Bio-Rad, Hercules, Calif.), 1 μM mix of forward and reverse primers, and 5 μL total RNA. A four-step protocol was used: denaturation, 3 minutes at 95° C.; amplification and quantification, 40 cycles of 15 seconds at 95° C. followed by 30 seconds at 60° C.; melting curve, 60 to 95° C. with a heating rate of 0.5° C. per second; followed by cooling (MyiQ Single Color Real-Time PCR Detection System; Bio-Rad). A single peak melting curve was observed for each gene product. Relative quantitative expression levels were determined for each gene. All results are displayed as an expression ratio normalized against β-actin expression levels using the $2^{-\Delta CT}$ method (FIG. 8).

Streptozotocin (STZ) induced diabetes. Twelve week old C57Bl/6 mice were used for this study. Mice were induced to have diabetes by intraperitoneal injection of 170 μg/g of streptozotocin (Sigma Aldrich, St. Louis, Mo.). Controls were injected with a vehicle (0.01M sodium citrate buffer). On the third day after STZ treatment, mice tail veins were bled to test the hyperglycemic status using blood sugar detection kit (Lifescan; Johnson & Johnson, Milpitas, Calif.). Mice with blood sugar levels of >300 mg/dL on the third day after STZ treatment were considered diabetic. Eye drop treatment containing 1% apoEdp or vehicle PBS was continued 4 times a day for 14 consecutive days. Intraperitoneal (i/p) injection containing 40 mg/kg of apoEdp or vehicle control PBS was administered once daily for 14 consecutive days. On the 15th day post-treatment, mice were euthanized, their eyes enucleated, and the retinas dissected out to use for mRNA or Western blot analysis.

Immunohistochemistry. Following euthanasia, enucleated mouse eyes were immersed in 10% buffered formalin and subsequently embedded in paraffin. Serial sections (6μ, thick) were prepared out of paraffin blocks. Following deparaffinization sections were hydrated by sequential immersion in xylene and graded alcohol solutions, and were treated with proteinase K for 5 minutes at 37° C. Sections were processed using immunohistochemistry kit (Pierce, Rockford, Ill.). Slides were incubated overnight at 4° C. with anti-ZO-1 (1:100; Santa Cruz Bio, CA) and donkey anti-rabbit IgG (1:400, Santa Cruz Bio, CA) secondary antibodies. The slides were mounted in aqueous mounting medium (supplied with kit) and observed by light microscopy (Carl Zeiss Meditec, Chester, Va.).

Statistical Analysis. Statistical differences between groups were evaluated with the Student unpaired t-test (two-tailed). Mean±SD is shown. $P \leq 0.05$ was considered significant.

Example 1

ApoEdp protects the loss of tight junction protein occludin of human retinal endothelial cells maintained in high glucose environments.

Figure 5:
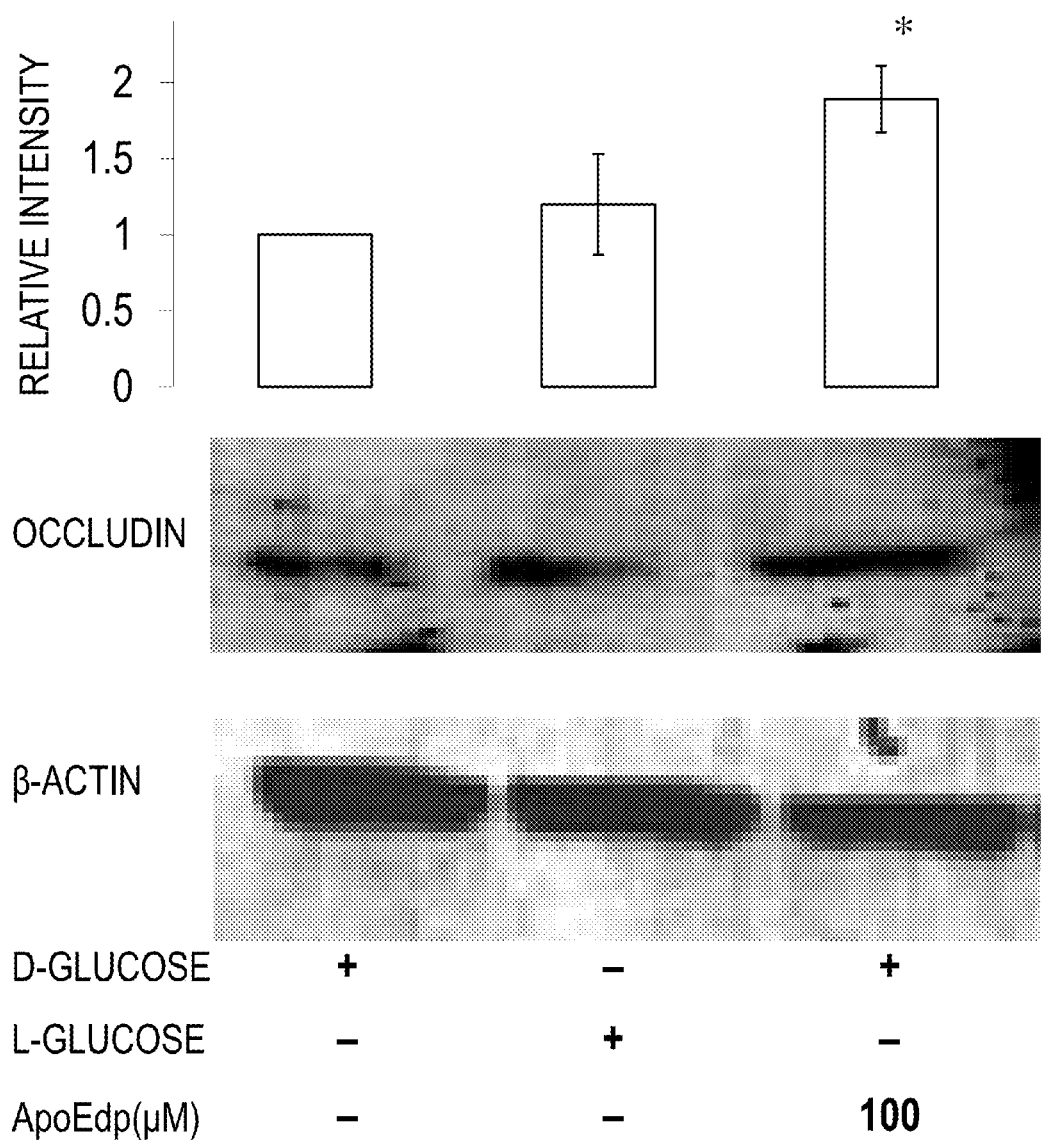
FIG. 5 shows that apoEdp inhibits high glucose-induced loss of occludin expression in human retinal endothelial cells.

There is a paucity of information about the cell types involved in the control of endothelium blood-retinal barrier (BRB) properties and whether apoE deficiency alters BRB permeability. The BRB is formed by retinal endothelial cells, and is essential for the protection of retina from harmful agents in the blood (18). RE (retinal endothelial) cells form tight junctions (TJs) that are essential for maintaining the structural integrity of BRB (19). The assembly of BRB tight junctions requires at least three types of transmembrane proteins, including Occludin, claudin and other retinal TJ proteins (18,19). As shown in FIG. 5, incubation of human retinal microvascular endothelial cells (hRMECs) with 30 mM of D- or L-glucose was associated with lower levels of occludin expression than that seen when the cells were incubated with both 30 mM of D-glucose and 100 μM apoEdp. Thus, apoEdp may prevent the suppression of occludin expression caused by D- or L-glucose and/or enhance the expression of occludin.

Example 2

Figure 4:
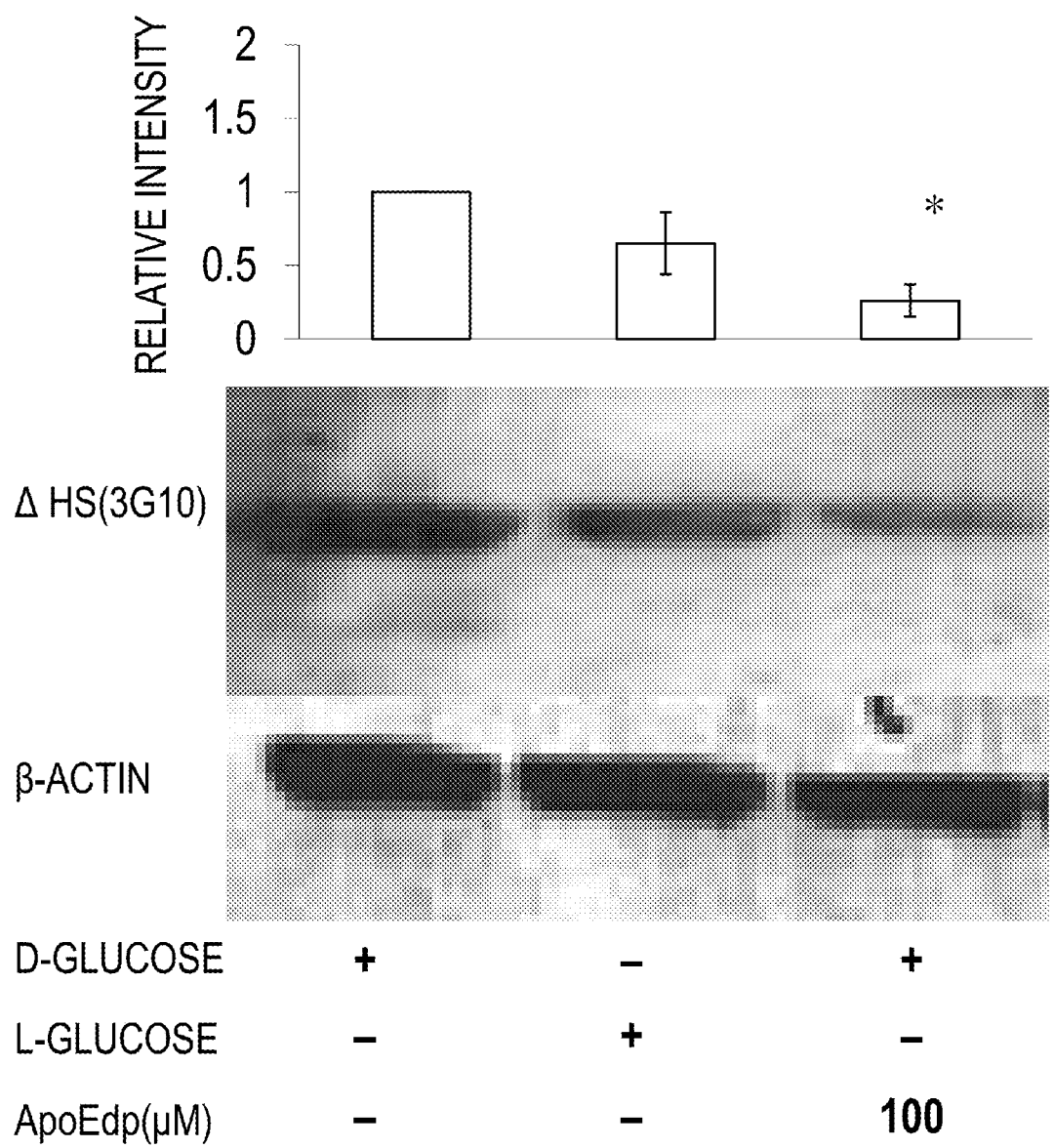
FIG. 4 shows that apoEdp inhibits high glucose-induced shedding of heparan sulfate (HS) in human retinal endothelial cells.
Figure 6:
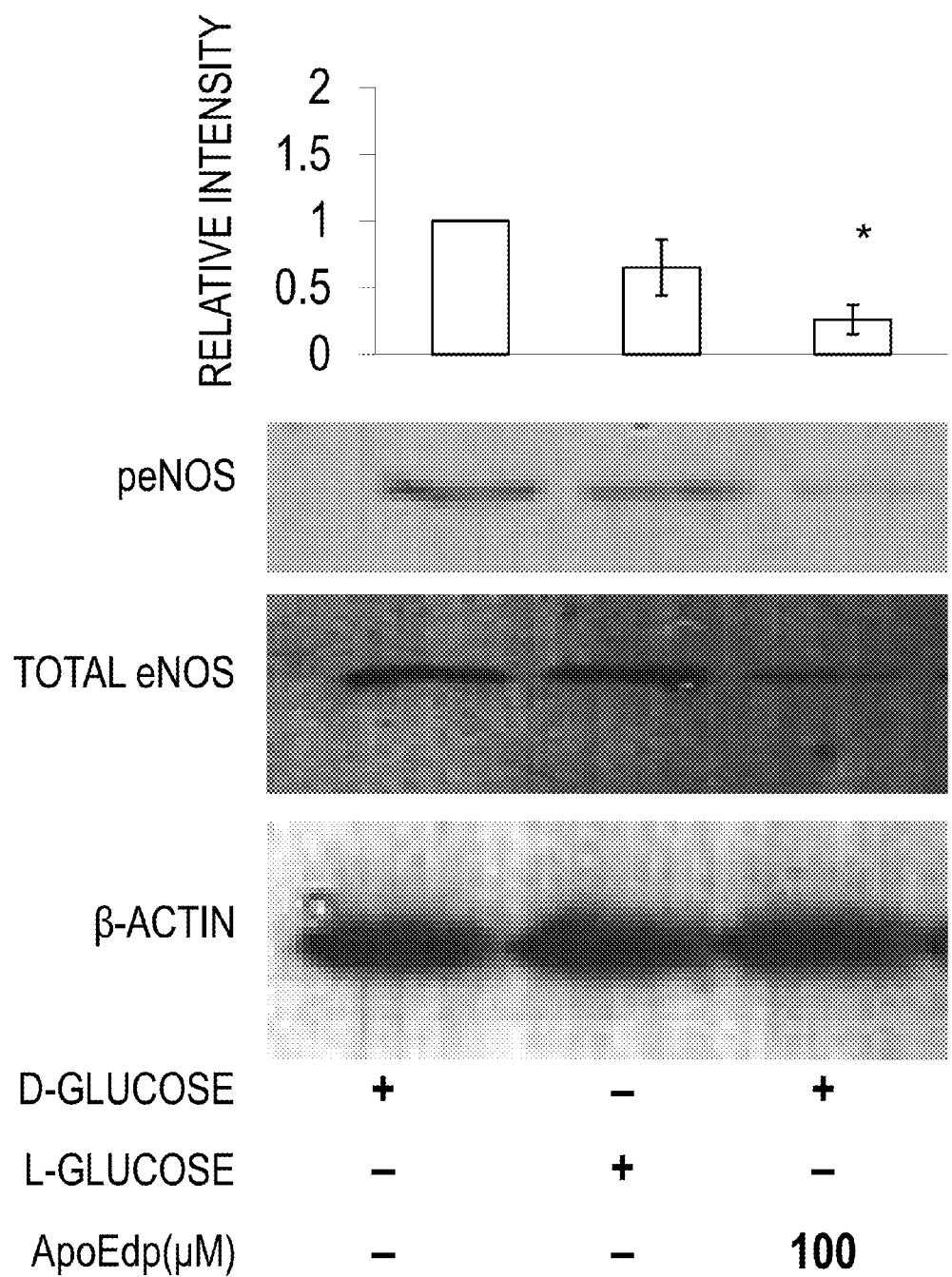
FIG. 6 shows that apoEdp inhibits high glucose-induced expression of eNOS in human retinal endothelial cells.

ApoEdp inhibits high glucose-induced expression of eNOS, heparanase, and MMP9 in vitro. Treatment of human retinal microvascular endothelial cells (hRMECs) with 30 mM D-glucose led to elevated expression of endothelial nitric oxide synthase (eNOS), which was prevented by 30 minute treatment with 100 μM apoEdp (FIG. 6). High glucose (30 mM) treatment of hRMECs for 72 hours induced elevated expression of ECM-degrading enzymes heparanase (FIG. 2) and MMP9 (FIG. 3), and resulted in increased shedding of heparan sulfate (HS) (FIG. 4) and the tight junction protein occludin (FIG. 5). Treatment of hRMECs with 50 or 100 μM of apoEdp suppressed the expression of heparanase and MMP9 (FIGS. 2 & 3, respectively), and reduced the shedding of HS and loss of tight junction protein occludin (FIGS. 4 & 5, respectively).

Example 3

ApoEdp is a cornea-penetrating peptide.

The apoEdp peptide (SEQ ID NO:3) is rich in cationic amino acids, and the inventor postulated that it may cross the cornea into the anterior and posterior chambers of the eye. To test this hypothesis, corneal permeability studies of apoEdp in mice (results shown in TABLE 1) were performed. The results demonstrate that apoEdp is a cornea-penetrating peptide. Thus, apoEdp can be used for non-invasive treatment of posterior eye diseases.

A one percent (1%) solution comprising apoEdp in PBS was prepared. This solution was applied bilaterally via eyedropper to the eyes of mice (n=4). The mice were sacrificed at 0, 1, 2, or 3 hours after application of the solution, and the eyes were enucleated. The aqueous and vitreous humor from each eye was collected and pooled, mixed with 1 mL of 0.1% formic acid solution, and allowed to stand for 5 minutes. The samples were then filtered with a 0.2 µm filter and analyzed with the Acquity UPLC system (Waters Corp., Milford, Mass.) with mass spectrophotometric detection. Results from the run are shown in TABLE 1.

TABLE 1

| OS | | | OD | | |
|---|---|---|---|---|---|
| Time (h) | Meas'd conc. (µg/ml) | Total (ng) | Time (h) | Meas'd conc. (µg/ml) | Total (ng) |
| 0 | * | * | 0 | * | * |
| 1 | * | * | 1 | 0.022 | 22.2 |
| 2 | 0.004 | 3.89 | 2 | 0.006 | 5.9 |
| 3 | 0.058 | 58.08 | 3 | 0.036 | 36.3 |

OS: left eye; OD: right eye; h: hour;
* No peak detected.

As demonstrated by the data of TABLE 1, topically-applied apoEdp can be detected inside the eye in as little as one hour after application, and the concentration of apoEdp inside the treated eye increases with time. These data demonstrate that apoEdp is a cornea-penetrating peptide, and show that topically-applied apoEdp is available for activity at the retina.

Initially, the mass range for the peptide was scanned several peaks corresponding to different charged states of the peptide were found. These peaks included 484.9 m/z, 604.4 m/z, and 805.6 m/z. The 484.9 peak was used for the analysis because it was the strongest peak. For the UPLC analysis, a 2.1 mm×100 mm×1.7 µm BEH300 C4 column was used. A two-component mobile phase was used with component 1 (C1): 0.1% formic Acid, and Component 2 (C2): Acetonitrile with 0.1% formic acid. The flow rate was 0.2 mL/min and gradient elution was used with a linear gradient (see TABLE 2). Retention time for the peptide was 4.6 minutes.

TABLE 2

| Time (min) | Flow (ml/min) | C1 % | C2 % |
|---|---|---|---|
| 0 | 0.2 | 90 | 10 |
| 2 | 0.2 | 90 | 10 |
| 12 | 0.2 | 20 | 80 |
| 12.01 | 0.2 | 90 | 10 |
| 15 | 0.2 | 90 | 10 |

Example 4

ApoEdp suppresses laser photocoagulation-induced expression of heparanase and MMPs in mouse retinas in vivo.

Male C57BL/6 mice (6-8 weeks old) were subjected to laser photocoagulation-induced retinal injury. Vascular leakage was seen in the retina at 7 and 14 days after laser photocoagulation-induced retinal injury, but not in control retinas (in progress; data not shown). They were injected intraperitoneally with apoEdp at 40 mg/kg once each day for 7 days. Seven days after laser injury, the mice were euthanized, the retinas were collected, and RNA was extracted from the isolated retinas to evaluate gene expression of heparanase and MMPs by real time ΔΔRT-PCR. As shown by real-time quantitative RT-PCR, expression of MMP2, MMP9, and heparanase was significantly greater in retinas subjected to laser photocoagulation-induced retinal injury than that observed in control retinas. The data of FIG. 8 show that in the laser photocoagulation-induced retinal injury model, expression of MMP2, MMP9, and heparanase was dramatically reduced after treatment for 7 days with apoEdp, as compared with the retinas of mice that did not receive apoEdp. These data suggest that administration of apoEdp to a mammal (e.g., a human) would exert protective effects by, for example, suppressing the expression of MMPs and heparanase.

Example 5

Figure 9:
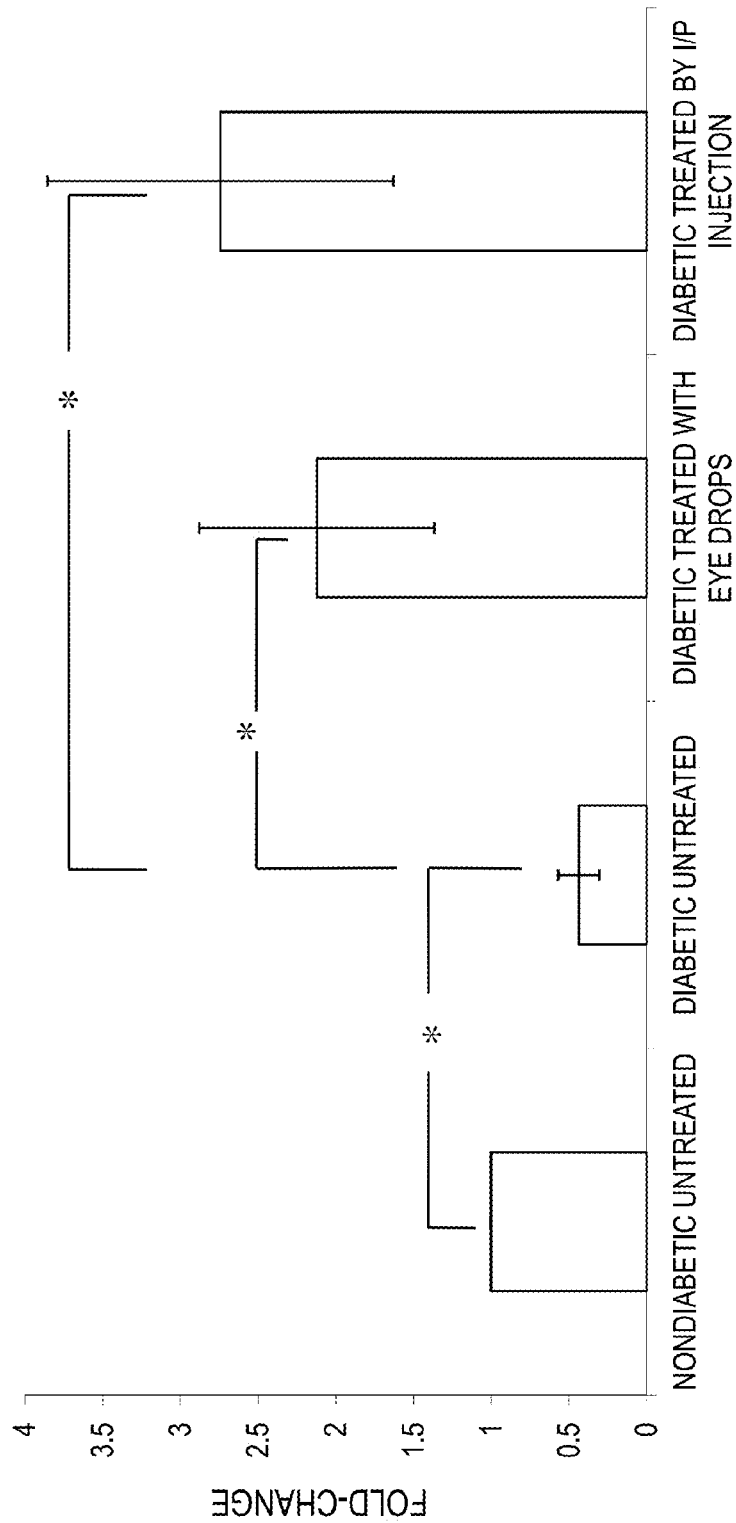
FIG. 9 shows real-time RT-PCR analysis of occludin mRNA expression in the retina of mice eyes following apoEdp treatment.
Figure 10:
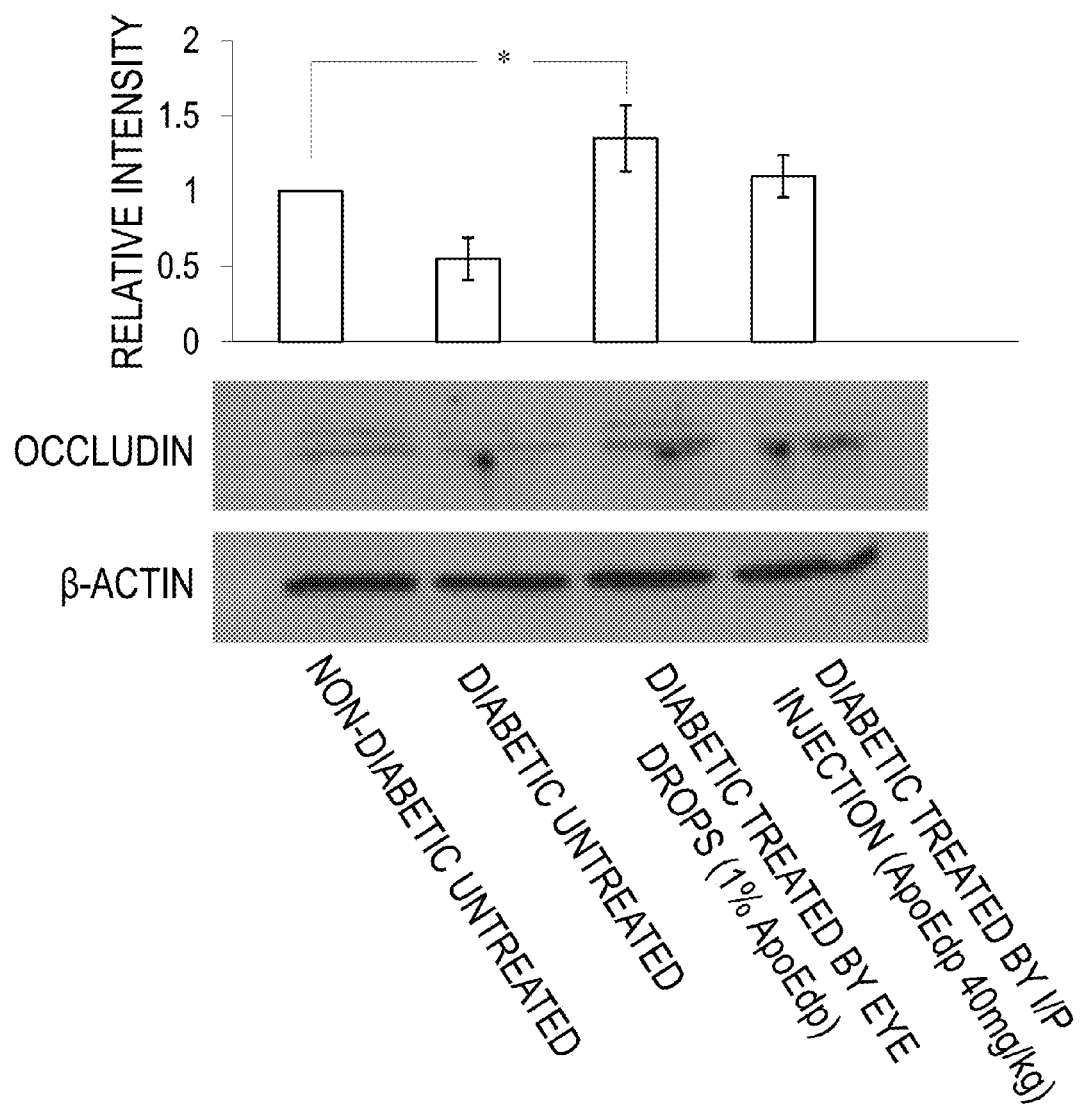
FIG. 10 shows Streptozotocin-induced diabetic mice treated for 14 consecutive days and Western blot analysis of tight junction protein occludin assayed in excised mice retinas.

ApoEdp Treatment Inhibits Loss of Retinal Tight Junction Proteins in Steptozotocin Induced Diabetic (Hyperglycemic) Mice To investigate the effects on the retinal tight junction protein occludin following topical eye drop (1% apoEdp) or systemic i/p injection (40 mg/kg) of apoEdp, retinas from enucleated mouse eyes were processed to harvest total RNA, and then one-step real-time RT-PCR was performed using mice occludin-specific mRNA expression. As shown in FIG. 9, both eye drop and i/p injection of apoEdp significantly inhibited the down-regulation of occludin-specific mRNA compared to diabetic non-treated mouse retinas. To correlate the occludin-specific mRNA data at a protein level, total proteins extracted from retinas of different experimental groups (FIG. 10) were analyzed using Western-blot to detect occludin-specific protein expression. As shown in FIG. 10, both eye drop and i/p injection of apoEdp significantly attenuated the loss of occludin in diabetic mice.

Example 6

ApoEdp treatment inhibits the loss of cell-to-cell adhesion type tight junction protein zona occludin 1 (ZO-1) specific protein expression in steptozotocin induced diabetic mouse retinas as determined by immunohistochemistry.

Figure 11:
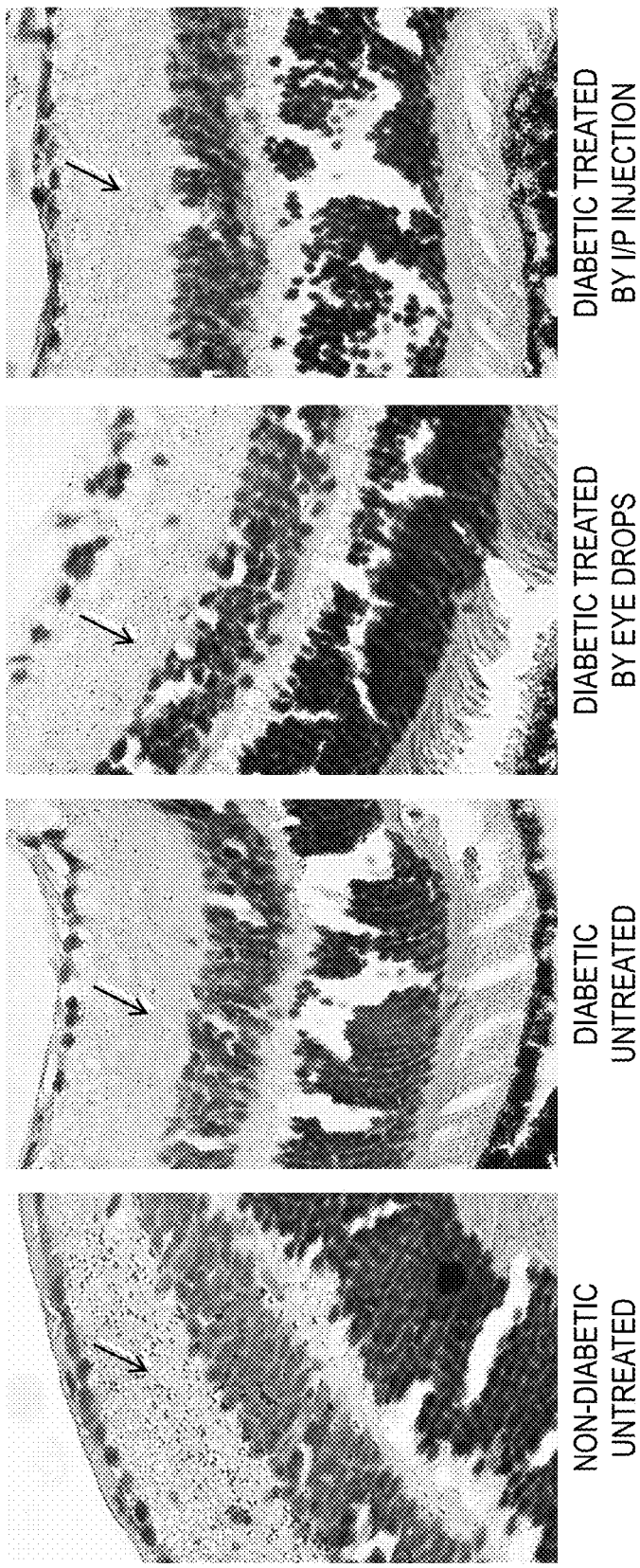
FIG. 11 shows immunohistochemical staining of mice retinas showing immunoreactivity of tight junction protein Zona occludin-1 (arrows).
Figure 12:
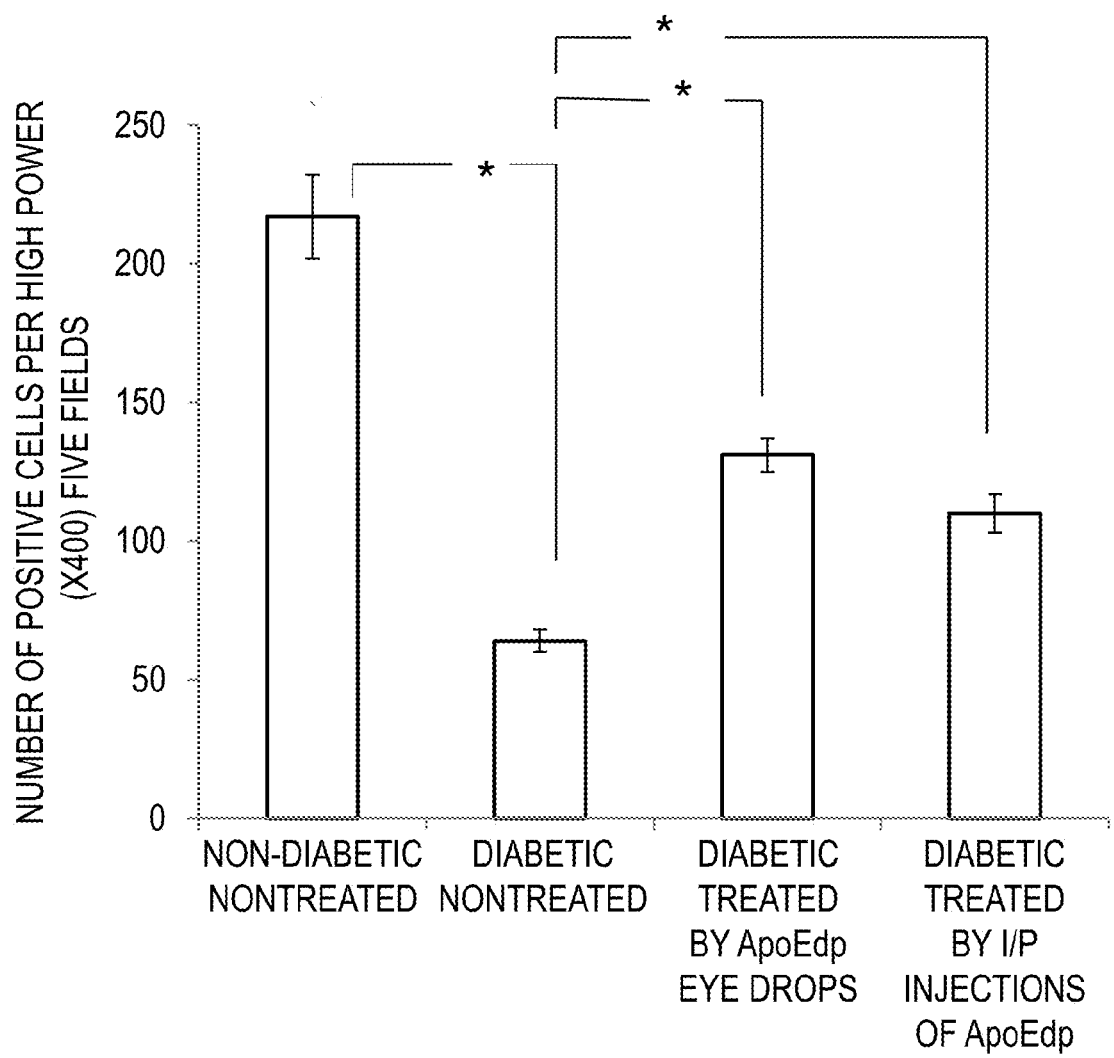
FIG. 12 shows immunohistochemical analysis of ZO-1 protein in mice retinas

To investigate the effect of apoEdp on attenuation of ZO-1 loss, immunohistochemical detection of ZO-1 was performed in formalin-fixed de-paraffinized sections of mouse retinas of different experimental groups. Initially, occludin-specific antibody was tried but, due to high non-specific background, data was not available. Instead, ZO-1 specific antibody was used. As shown in FIG. 11, cells expressing ZO-1 were identified by the arrows in the photos (FIG. 11). FIG. 12 is the immunohistochemical analysis of ZO-1 protein in mouse retinas. The number of positive cells was determined in the high-power field (×400) for the retinas.

The retinas of untreated diabetic mice had significantly fewer positive cells (p<0.05) than those of non-diabetic, untreated (normal) controls. Treatment with either topical 1% apoEdp drops or i/p injections of apoEdp (40 mg/kg) for 14 consecutive days significantly increased the number of positive cells compared to the untreated, diabetic retina.

Example 7

ApoEdp inhibits the up-regulated expression of VEGF in the retinas of diabetic mice.

Figure 13:
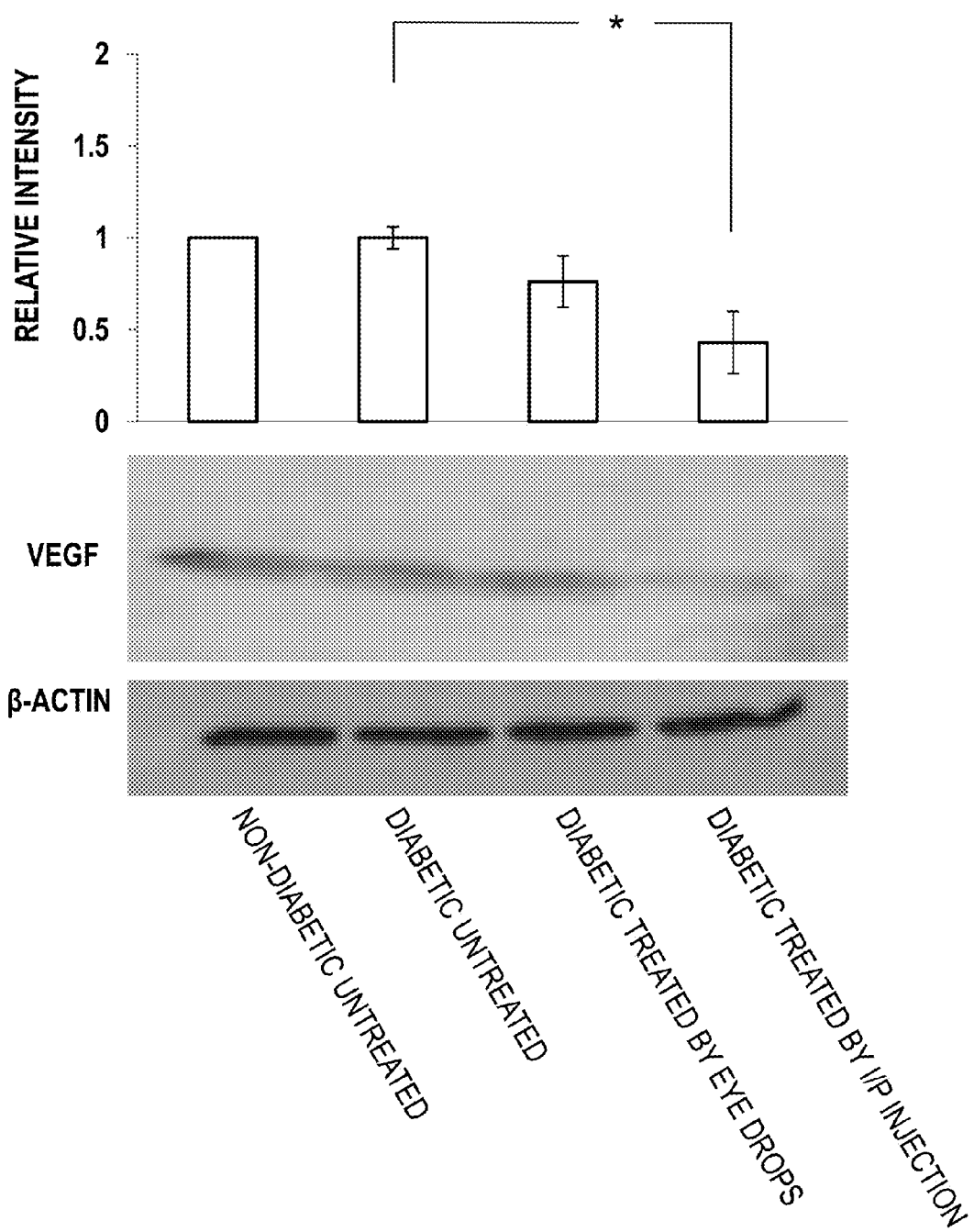
FIG. 13 shows Streptozotocin-induced diabetic mice treated for 14 consecutive days and Western blot analysis of VEGF protein assayed in excised mice retinas.

Upregulation of VEGF expression is reported as one of the reasons for the loss of tight junction proteins in diabetic mice (20). Western blot analysis of total proteins extracted from diabetic mouse retinas revealed significant inhibition of VEGF in the retinas of apoEdp treated diabetic mice compared to untreated diabetic mice (FIG. 13).

Thus, the data demonstrate that either 14-day eye drop application or systemic i/p injection of apoEdp reversed increased expression of heparanase and associated loss of HS and tight junction protein ZO-1. Increased vascular permeability in diabetic retinopathy (DR) is reported to result in a concomitant increase of VEGF. The VEGF pathway is known to play a role in breakdown of the BRB through a mechanism involving the down regulation of tight junction proteins in the retinal microvasculature (20). The results suggest that even via topical application by eye drops, apoEdp crossed the cornea to reach the interior chamber of the eyes. The i/p injection of apoEdp significantly reduced VEGF expression of retina compared to diabetic untreated. Although inhibition of VEGF by eye drop treatment was found, but it was not significantly different from untreated diabetic mice.

The results therefore are indicative of an innovative approach to non-invasive therapeutic strategies for treating diabetic vascular complications.

Example 8

ApoEdp inhibits upregulated LRP-1 expression in high sugar induced human retinal endothelial cells in vitro.

Low density lipoprotein receptor-related protein 1 (LRP1), also known as apolipoprotein E receptor (APOER) or cluster of differentiation 91 (CD91), is a protein forming a receptor found in the plasma membrane of cells involved in receptor-mediated endocytosis. LRP-1 belongs to the LDL receptor superfamily and is a large endocytic scavanger receptor. LRP-1 is expressed in almost every cell of the body, and is involved in internalization and subsequent endocytic processing of several proteolytic enzymes and growth factors. LRP-1 was first characterized as an endocytic receptor for apolipoprotein E (apoE)-containing lipoprotein particles (21). LRP-1 has a bifunctional role as endocytic receptor and to stimulate cell migration through regulation of several signaling pathways related to endothelial cell matrix (ECM) proteolysis. LRP-1 mediated degradation of ECM release matrix bound angiogenic growth factors VEGF. Thus, Applicant considered LRP-1 targeting as an attractive strategy for diabetic retinopathy treatment.

Figure 14:
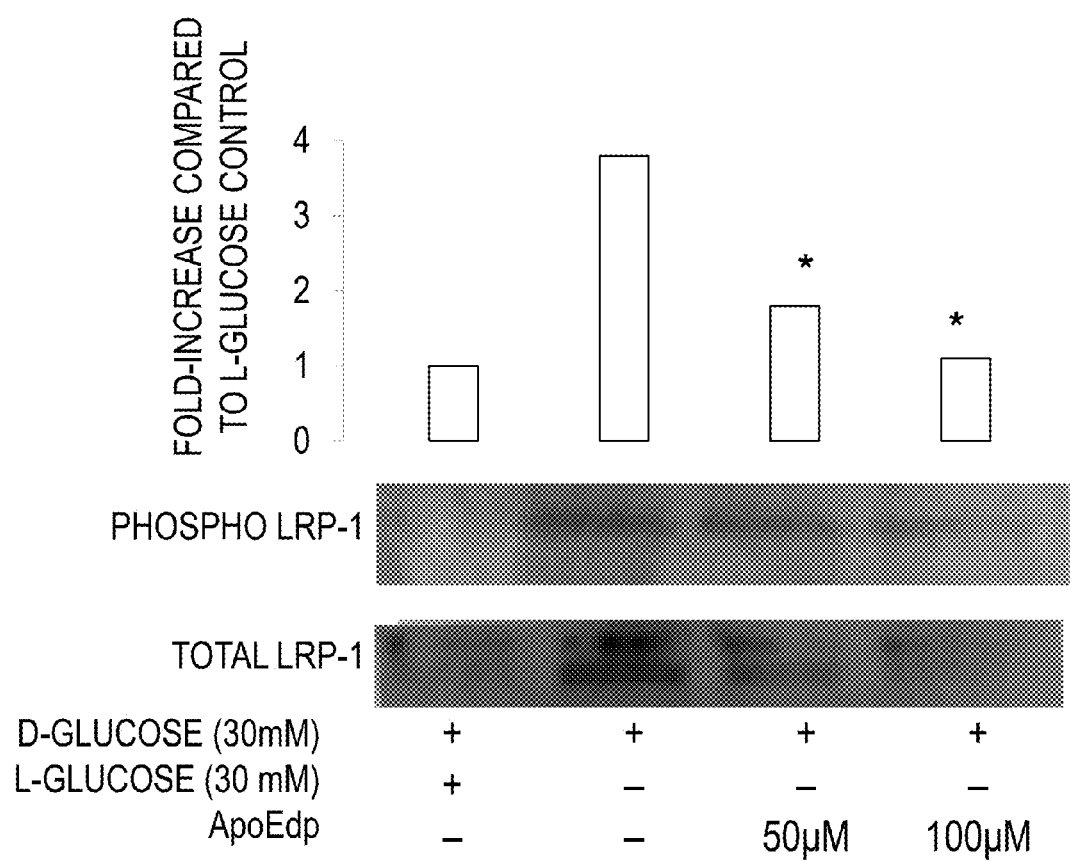
FIG. 14 shows apoEdp inhibition of upregulated LRP-1 expression in high sugar induced human retinal endothelial cells in vitro.

As shown in FIG. 14, 1% apoEdp treatment was capable of inhibiting the upregulation of LRP-1 in high sugar induced human retinal microvascular endothelial cells (hRMECs) cells. Using an anti-LRP-1 antibody (human LRP-1; 1:1000, Santa Cruz Biotechnology, CA) and Western blot analysis, selective inhibition of LRP-1 by apoEdp treatment (24 hours) in serum starved hRMECs cells was shown. The data of FIG. 14 demonstrate that apoEdp is a potent inhibitor of LRP-1 expression in high sugar induced hRMECs cells.

Figure 15:
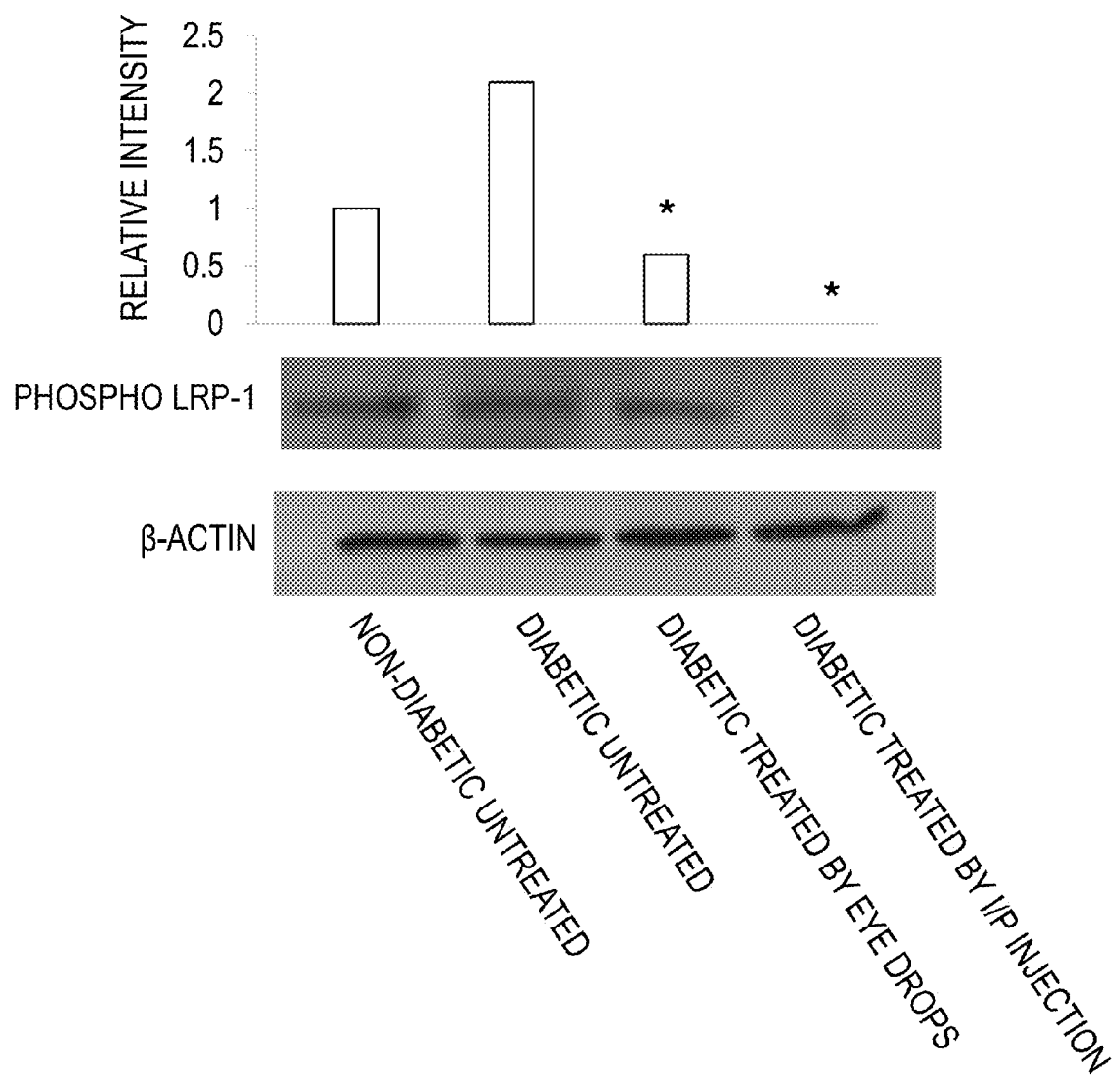
FIG. 15 shows that LRP-1 levels are elevated in retinas of streptozotocin-induced diabetic mice, versus controls, and 1% apoEdp administration, whether via eye drops or via intraperitoneal (i/p) injection caused significant reduction in retinal LRP-1 levels

As shown in FIG. 15, LRP-1 protein levels are elevated in retinas of streptozotocin-induced diabetic mice, versus controls, and 1% apoEdp administration, whether via eye drops or via intraperitoneal (i/p) injection caused significant reduction in retinal LRP-1 protein levels.

REFERENCES

1. Fong D S, Aiello L P, Ferris F L 3rd, Klein R. Diabetic retinopathy. Diabetes Care. 2004 October; 27(10):2540-53.
2. Mahley R W. Apolipoprotein E: cholesterol transport protein with expanding role in cell biology. Science. 1988 Apr. 29; 240(4852):622-30.
3. Weisgraber K H, Innerarity T L, Rall S C Jr, Mahley R W. Receptor interactions controlling lipoprotein metabolism. Can J Biochem Cell Biol. 1985 August; 63(8):898-905.
4. Ji Z S, Fazio S, Mahley R W. Variable heparan sulfate proteoglycan binding of apolipoprotein E variants may modulate the expression of type III hyperlipoproteinemia. J Biol Chem. 1994 May 6; 269(18):13421-8.
5. Dyer C A, Cistola D P, Parry G C, Curtiss L K. Structural features of synthetic peptides of apolipoprotein E that bind the LDL receptor. J Lipid Res. 1995 January; 36(1): 80-8.
6. Anderson D H, Ozaki S, Nealon M, Neitz J, Mullins R F, Hageman G S, Johnson L V. Local cellular sources of apolipoprotein E in the human retina and retinal pigmented epithelium: implications for the process of drusen formation. Am J Ophthalmol. 2001 June; 131(6):767-81.
7. Xu H Z, Le Y Z. Significance of outer blood-retina barrier breakdown in diabetes and ischemia. Invest Ophthalmol Vis Sci. 2011 Apr. 5; 52(5):2160-4.
8. Parish C R, Freeman C, Hulett M D. Heparanase: a key enzyme involved in cell invasion. Biochim Biophys Acta. 2001 Mar. 21; 1471(3):M99-108.
9. Elkin M, Ilan N, Ishai-Michaeli R, Friedmann Y, Papo O, Pecker I, Vlodaysky I. Heparanase as mediator of angiogenesis: mode of action. FASEB J. 2001 July; 15(9):1661-3.
10. Dredge K, Hammond E, Handley P, Gonda T J, Smith M T, Vincent C, Brandt R, Ferro V, Bytheway I. PG545, a dual heparanase and angiogenesis inhibitor, induces potent anti-tumour and anti-metastatic efficacy in preclinical models. Br J Cancer. 2011 Feb. 15; 104(4):635-42.
11. Raman K, Ninomiya M, Nguyen T K, Tsuzuki Y, Koketsu M, Kuberan B. Novel glycosaminoglycan biosynthetic inhibitors affect tumor-associated angiogenesis. Biochem Biophys Res Commun. 2011 Jan. 7; 404(1):86-9.
12. Huet E, Vallée B, Delbé J, Mourah S, Pruliere-Escabasse V, Tremouilleres M, Kadomatsu K, Doan S, Baudouin C, Menashi S, Gabison E E. EMMPRIN modulates epithelial barrier function through a MMP-mediated occludin cleavage: implications in dry eye disease. Am J Pathol. 2011 September; 179(3):1278-86.
13. Kowluru R A. Role of matrix metalloproteinase-9 in the development of diabetic retinopathy and its regulation by H-Ras. Invest Ophthalmol Vis Sci. 2010 August; 51(8): 4320-6.
14. Bhatt L K, Addepalli V. Attenuation of diabetic retinopathy by enhanced inhibition of MMP-2 and MMP-9 using aspirin and minocycline in streptozotocin-diabetic rats. *Am J Transl Res.* 2010 Feb. 12; 2(2):181-9.
15. Klein R, Davis M D, Moss S E, Klein B E, DeMets D L. The Wisconsin Epidemiologic Study of Diabetic Retinopathy. A comparison of retinopathy in younger and older onset diabetic persons. Adv Exp Med Biol. 1985; 189:321-35.
16. Kelley B A, Neil S J, McKnight A, Santos J M, Sinnis P, Jack E R, Middleton D A, Dobson C B. Apolipoprotein E-derived antimicrobial peptide analogues with altered membrane affinity and increased potency and breadth of activity. FEBS Journal. 2007; 274:4511-4525.
17. Bhattacharjee P S, Huq T S, Mandal T K, Graves R A, Muniruzzaman S, Clement C, McFerrin H E, Hill J M. A novel peptide derived from human apolipoprotein E is an inhibitor of tumor growth and ocular angiogenesis. PLoS One. 2011; 6(1):e15905.
18. Xu H Z, Le Y Z. Significance of outer blood-retina barrier breakdown in diabetes and ischemia. Invest Ophthalmol Vis Sci. 2011 Apr. 5; 52(5):2160-4.
19. Rao R. Occludin phosphorylation in regulation of epithelial tight junctions. Ann N Y Acad Sci. 2009 May; 1165:62-8.
20. Miyamoto K, Khosrof S, Bursell S E, Moromizato Y, Aiello L P, et al. Vascular endothelial growth factor (VEGF)-induced retinal vascular permeability is mediated by intercellular adhesion molecule-1 (ICAM-1). *Am J Pathol.* 2000; 156:1733-1739.
21. Kowal R C, Herz J, Goldstein J L, Esser V, Brown M S. Low density lipoprotein receptor-related protein mediates uptake of cholesteryl esters derived from apoprotein E-enriched lipoproteins. *Proc. Natl. Acad. Sci. U.S.A.* 1989; 86(15):5810-4.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

What is claimed is:

1. A method for treating retinopathy in a mammal in need thereof, comprising providing a pharmaceutical composition to said mammal, wherein the pharmaceutical composition comprises the human apolipoprotein E derived dimer peptide (apoEdp) having the sequence of SEQ ID NO:3, wherein said pharmaceutical composition is provided systemically.

2. The method of claim 1, wherein said retinopathy is diabetic retinopathy.

* * * * *

UNITED STATES PATENT AND TRADEMARK OFFICE
CERTIFICATE OF CORRECTION

| | | |
|---|---|---|
| PATENT NO. | : 9,636,299 B2 | Page 1 of 1 |
| APPLICATION NO. | : 14/388412 | |
| DATED | : May 2, 2017 | |
| INVENTOR(S) | : Partha S. Bhattacharjee | |

It is certified that error appears in the above-identified patent and that said Letters Patent is hereby corrected as shown below:

At Column 1, below the title, please add:
    -- STATEMENT REGARDING FEDERALLY SPONSORED RESEARCH OR DEVELOPMENT
    This Invention was made with U.S. Government support under Contract No. 1R21EY019144-01
    awarded by the National Eye Institute. The Government has certain rights in this invention. --

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 3

<210> SEQ ID NO 1
<211> LENGTH: 18
<212> TYPE: PRT
<213> ORGANISM: Homo sapiens
<220> FEATURE:
<221> NAME/KEY: BINDING
<222> LOCATION: (1)..(18)
<223> OTHER INFORMATION: amino acids 133-150 of mature apoE,
      corresponding to receptor binding domain

<400> SEQUENCE: 1

Leu Arg Val Arg Leu Ala Ser His Leu Arg Lys Leu Arg Lys Arg Leu
1               5                   10                  15

Leu Arg

<210> SEQ ID NO 2
<211> LENGTH: 17
<212> TYPE: PRT
<213> ORGANISM: Homo sapiens
<220> FEATURE:
<221> NAME/KEY: BINDING
<222> LOCATION: (1)..(17)
<223> OTHER INFORMATION: amino acids 133-149 of mature apoE,
      corresponding to heparan sulfate binding domain

<400> SEQUENCE: 2

Leu Arg Val Arg Leu Ala Ser His Leu Arg Lys Leu Arg Lys Arg Leu
1               5                   10                  15

Leu

<210> SEQ ID NO 3
<211> LENGTH: 18
<212> TYPE: PRT
<213> ORGANISM: Artificial Sequence
<220> FEATURE:
<223> OTHER INFORMATION: Artificial apoEdp amino acid sequence
```

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (18)..(18)
<223> OTHER INFORMATION: AMIDATION

<400> SEQUENCE: 3

Leu Arg Lys Leu Arg Lys Arg Leu Leu Leu Arg Lys Leu Arg Lys Arg
1               5                   10                  15

Leu Leu
```